US006432652B1

(12) United States Patent
Evans et al.

(10) Patent No.: US 6,432,652 B1
(45) Date of Patent: *Aug. 13, 2002

(54) METHODS OF SCREENING MODULATORS OF OPIOID RECEPTOR ACTIVITY

(75) Inventors: Christopher J. Evans, Venice; Duane E. Keith, Jr., Woodland Hills; Robert H. Edwards, Los Angeles; Daniel Kaufman, Santa Monica, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/405,271

(22) Filed: Mar. 14, 1995

Related U.S. Application Data

(63) Continuation-in-part of application No. 08/403,260, filed on Mar. 13, 1995, now abandoned, which is a continuation-in-part of application No. 08/387,707, filed as application No. PCT/US93/07665 on Aug. 13, 1993, now Pat. No. 6,265,563, which is a continuation-in-part of application No. 07/929,200, filed on Aug. 13, 1992, now abandoned.

(51) Int. Cl.[7] ...................... G01N 33/53; G01N 33/567; C12P 21/06; C12P 21/04
(52) U.S. Cl. ........................ 435/7.2; 435/7.1; 435/69.1; 435/70.1; 435/71.1; 435/71.2
(58) Field of Search .......... 435/7.1, 7.2, 69.1, 435/320, 71.1, 70.1, 71.2; 536/23.5

(56) References Cited

PUBLICATIONS

Mansson et al., Biochem and Biophys. Research Commun., 202, 1431–1437, Aug. 1994.*
Chen et al., Biochem. J., 295, 625–628, 1993.*
Yasuda, K. et al. PNAS 90:6736–6740, 1993.*
Akiyama et al., *Proc. Natl. Acad. Sci. USA*, vol. 82, pp. 2543–2547 (1985).
Bochet et al., *Molecular Pharmacology*, vol. 34, pp. 436–443 (1988).
Carr et al., *Immunology Letters*, vol. 20, No. 3, pp. 181–186 (1989).
Davis et al., "Basic Methods in Molecular Biology,"Elsevier Science Publishing Co., Inc., New York, pp. 1–372 (Table of Contents provided), 1996.
Eberwine et al., Federation Proceedings, vol. 46, No. 4, p. 1444, abstract No. 6582 (1987).
Erspamer et al., *Proc. Natl. Acad. Sci. USA*, vol. 86, pp. 5188–5192 (1989).
Evans et al, *Society for Neuroscience Abstracts*, vol. 18, Part 1, p. 21, abstract 16.1 (1992).
Evans et al., *Science*, vol. 258, pp. 1952–1955 (1992).

Garcel et al., *FEBS Letters*, vol. 118, pp. 245–247 (1980).
Gilbert et al, *J. Pharmacol. Exp. Ther.*, vol. 198, pp. 66–82 (1976).
Goodman and Gilman's *The Pharmacological Basis of Therapeutics*, 7th ed., pp. 493–495 (MacMillan 1985).
Gross et al., *Proc. Natl. Acad. Sci. USA*, vol. 87, pp. 7025–7029 (1990).
Kieffer et al., *Proc. Natl. Acad. Sci. USA*, vol. 89, pp. 12048–12052 (1992).
Klee et al., *Proc. Natl. Acad. Sci. USA*, vol. 71, pp. 3474–3477 (1974).
Langord et al., *Biochem. Biophys. Res. Comm.*, vol. 138, pp. 1025–1032 (1992).
Law et al., *Molecular Pharmacology*, vol. 21, pp. 438–491 (1982).
Lord et al., *Nature*, vol. 267, pp. 495–499 (1977).
Louie et al., *Biochem. Biophys. Res. Comm.*, vol. 152, pp. 1369–1375 (1988).
Mansour et al., *Trends in Neurosci.*, vol. 11, pp. 308–314 (1988).
Mulder et al., *Eur. J. Pharmacol.*, vol. 205, pp. 1–6 (1991).
Negri et al., *Eur. J. Pharmacol.*, vol. 196, pp. 335–336 (1991).
Pert et al., *Science*, vol. 179, pp. 1011–1014 (1973).
Sanger et al., *Proc. Natl. Acad. Sci. USA*, vol. 74, No. 12, pp. 5463–5467 (1977).
Schofield et al., *The Embo Journal*, vol. 8(2), pp. 489–495 (1989).
Sharma et al., *Proc. Natl. Acad. Sci. USA*, vol. 72, pp. 3092–3096 (1975).
Sofuoglu et al., *Pharmacologist*, vol. 32, pp. 151 (1990).
Strosberg, A.D., *Eur. J. Biochem.*, vol. 196, pp. 1–10, Abstract No. 185 (1991).
Takemori et al., *Ann. Rev. Pharm. Toxicol.*, vol. 32, pp. 239–269 (1992).
Terenius, L., *Eur. J. Pharmacol.*, vol. 38, p. 211 (1976).
Tsunoo et al., *Proc. Natl. Acad. Sci. USA*, vol. 83, pp. 9832–9836 (1986).
Wollemann, M., *J. Neurochem.*, vol. 54, pp. 1095–1101 (1990).
Xie et al., *Proc. Natl. Acad. Sci. USA*, vol. 89, pp. 4124–4128 (1992).
Yasuda et al., *Proc. Natl. Acad. Sci. USA*, vol. 90, pp. 6736–6740 (1993).
Yu et al., *J. of Biol. Chem.*, vol. 261, No. 3, pp. 1065–1070 (1986).

(List continued on next page.)

*Primary Examiner*—Gary L. Kunz
*Assistant Examiner*—Robert S. Landsman
(74) *Attorney, Agent, or Firm*—Morrison & Foerster, LLP

(57) ABSTRACT

Genes encoding opioid receptors (including opioid-like receptor (ORL) proteins) can be retrieved from vertebrate libraries using the murine probe disclosed herein under low-stringency conditions. The DNA sequence shown in FIG. 5 or its complement can be used to obtain the human delta, kappa and mu genes as well as the murine mu gene and human ORL-1. The probe provided encodes the murine delta opioid receptor.

3 Claims, 26 Drawing Sheets

OTHER PUBLICATIONS

Mollereau, C. et al. "ORL1, a novel member of the opioid receptor family—Cloning, functional expression and localization" *FEBS Letters*, vol. 341, pp.33–38 (1994).

O'Dowd, B.F. et al., *GENE*, vol. 136, pp. 355–360, 1993.

Keith, Duane et al. "Isolation of cDNA Clones Homologous To Opioid Receptors" *Regulatory Peptides*, vol. 54, p. 143 (1994).

Gramsch et al., "Monoclonal Anti–idiotypic Antibodies to Opioid Receptors," *Jour of Biological Chem*, vol. 263, No. 12, pp. 5853–5859 (1988).

Machida et al., "Three Technical Approaches for Cloning Opioid Receptors," *Natl Institute on Drug Abuse Research Monograph Series*, pp. 93–110, (1988).

Simonds et al., "Purification of the opiate receptor of NG108–15 neuroblastoma–glioma hybrid cells," *Proc. Natl. Acad. Sci.*, vol. 82, pp. 4974–4978 (1985).

Smith et al, "Problems and Approaches in Studying Membrane Opioid Receptors," *Natl Institute on Drug Abuse Research Monograph Series*, pp. 69–84, (1991).

* cited by examiner

```
GCACGGTGGAGACGGACACGGGCGGCCATG GAG CTG GTG CCC TCT GCC CGT GCG GAG CTG CAG TCC TCG CCC CTC
                               Met Glu Leu Val Pro Ser Ala Arg Ala Glu Leu Gln Ser Ser Pro Leu

GTC AAC CTC TCG GAC GCC TTT CCC AGC GCC TTC CCC AGC GCC GCG GGC AAT GCG TCG GGG TCG CCG GGA
Val Asn*Leu Ser Asp Ala Phe Pro Ser Ala Phe Pro Ser Ala Gly Ala Asn*Ala Ser Gly Ser Pro Gly

GCC CGT AGT GCC TCG TCC CTC GCC CTA GCC ATC GCC ATC GCC CTC TAC TCG GCT GTG TGC GCA GTG
Ala Arg Ser Ala Ser Ser Leu Ala Leu Ala Ile Ala Ile Ala Leu Tyr Ser Ala Val Cys Ala Val

GGG CTT GGC AAC GTG CTC GTC ATG TTT GGC ATC GTC CGG TAC GTC AAA TTG AAG ACC ACC GCC AAC
Gly Leu Gly Asn Val Leu Val Met Phe Gly Ile Val Arg Tyr Thr Lys Leu Lys Thr Ala Asn

ATC TAC ATC TTC AAT CTG GCT TTG GCT GAT GCG CTG GCC ACG CTG CCC TTC CAG AGC GCC AAG
Ile Tyr Ile Phe Asn Leu Ala Leu Ala Asp Ala Leu Ala Thr Leu Pro Phe Gln Ser Ala Lys

TAC TTG ATG GAA ACG TGG CCG TTT GGC GAG CTG TGC AAG GCT GTG GTC TCC ATT GCT GTC TAC TAC AAC
Tyr Leu Met Glu Thr Trp Pro Phe Gly Glu Leu Cys Lys Ala Val Ser Ile Ala Val Cys Tyr Tyr Asn

ATG TTC ACT AGC ATC TTC ACC CTC ACC ATG AGC ATG AGC GTG GAC CGC TAC ATT GCT GTC TGC CAT CCT GTC
Met Phe Thr Ser Ile Phe Thr Leu Thr Met Ser Met Ser Val Asp Arg Tyr Ile Ala Val Cys His Pro Val

AAA GCC CTG GAC TTC CGG ACA CCA GCC AAG GCC AAG CTG ATC AAT ATA TGC ATC TGG ATC TTG GCT TCA
Lys Ala Leu Asp Phe Arg Thr Pro Ala Lys Ala Lys Leu Ile Asn Ile Cys Ile Trp Ile Leu Ala Ser

GGT GTC GGG GTC CCC ATC ATG GTC ATG GCA GTG ACC CAA CCC CGG GAT GGT GCA GTG GTA TGC ATG CTC
Gly Val Gly Val Pro Ile Met Val Met Ala Val Thr Gln Pro Arg Asp Gly Ala Val Val Cys Met Leu
```

FIG.5a

| CAG Gln | TTC Phe | CCC Pro | AGT Ser | CCC Pro | AGC Ser | TGG Trp | TAC Tyr | TGG Trp | GAC Asp | ACT Thr | GTG Val | ACC Thr | AAG Lys | ATC Ile | TGC Cys | GTG Val | TTC Phe | CTC Leu | TTT Phe | GCC Ala | TTC Phe | GTG Val |
| GTG Val | CCG Pro | ATC Ile | CTC Leu | ATC Ile | ACG Thr | GTG Val | TGC Cys | TAT Tyr | GGC Gly | CTC Leu | ATG Met | CTA Leu | CTG Leu | CGC Arg | AGC Ser | GTG Val | CGT Arg | CTG Leu | CTG Leu |
| TCC Ser | GGT Gly | TCC Ser | AAG Lys | GAG Glu | AAG Lys | GAC Asp | CGC Arg | AGC Ser | CTG Leu | CGG Arg | CGC Arg | ATG Met | ACG Thr | CGC Arg | ATG Met | GTG Val | CTG Leu | GTG Val | GTG Val | GGC Gly | GCC Ala |
| TTC Phe | GTG Val | GTG Val | TGC Cys | GCG Ala | CCC Pro | ATC Ile | CAC His | ATC Ile | TTC Phe | GTC Val | ATC Ile | TGG Trp | ACG Th

```
        *20                    *       40
MELVPSARAELQSSPLVNLSDAFPSAFPSAGANASGSPGARSAS--SLALAIAITALYSA
         MELTSEQFNGSQVWIPSPFDLNGSLGPSNGSNQTEPYYDMTSNAVLTFIYFV 60             80              100
VCAVGLLGNVLVMFGIVRYTKLKTATNIYIFNLALADALATSTLPFQSAKYLMETWPFGE
VCVVGLCGNTLVIYVILRYAKMKTITNIYILNLAIADELFMLGLPFLAMQVALVHWPFGK 120            140              160
 LLCKAVLSIDYYNMFTSIFTLTMMSVDRYIAVCHPVKALDFRTPAKAKLINICIWVLASG
AICRVVMTVDGINQFTSIFCLTVMSIDRYLAVVHPIKSAKWRRPRTAKMINVAVWGVSLI 180             200             220
VGVPIMVMAVTQPRD-GAVVCMLQFPSPSWYWDTVTKICVFLFAFVVPILIITVCYGLML
VILPIMIYAGLRSNQWGRSSCTINWPGESGAWYTGFIIYAFILGFLVPLTIICLCYLFII 240            260              280
LRLRSVRLLSGSKEKDRSLRRITRMVLVVVGAFVVCWAPIHIFVIVWTLVDINRRDPLVV
IKVKSSGIRVGSSKRKKSEKKVTRMVSIVVAVFIFCWLPFYIFNVSSVSVAIS-PTPALK 300            320              340
AALHLCIALGYANSSLNPVLYAFLDENFKRCFRQ-LCRTPCGRQEPGSLRRPRQATTRER
GMFDFVVILTYANSCANPILYAFLSDNFKKSFQNVLCLVKVSGAEDGERSDKQDKSRLN 360    370
VTACTPSDGPGGGAAA

ETTETQRTLLNGDLQTSI (SEQ ID NO:9)
```

FIG.6

HUMAN DELTA

Sequence Range: -131 to -1
```
                       -122*        -112*        -102*        -92*         -82*
Tuyet's H3  -GG GCA GTG TGC GTG TGC ATG CTC CAG TTC CCC AGC CCC AGC TGG TAC TGG GAC ACG
             610                 620                 630                 640          650                 660
DOR-1       gGt GCA GTG GTa GTa TGC ATG CTC CAG TTC CCC AGt CCC AGC TGG TAC TGG GAC ACt>
[ 478 ]     <^^ ^^^ ^^^ ^^v ^^v ^^^ ^^^ ^^^ ^^^ ^^^ ^^^ ^^v ^^^ ^^^ ^^^ ^^^ ^^^ ^^^ ^^v -72*         -62*         -52*         -42*         -32*
Tuyet's H3  GTG ACC AAG ATC TGC GTG TTC CTC TTC GCC TTC GTG GTG CCC ATC CTC ATC ATC
                                670                 680                 690                 700         710
DOR-1       GTG ACC AAG ATC TGC GTG TTC CTC TTC GCC TTt GCC TTC GTG GTG CCg ATC CTC ATC ATC>
[ 478 ]     ^^^ ^^^ ^^^ ^^^ ^^^ ^^^ ^^^ ^^^ ^^^ ^^^ ^^v ^^v ^^^ ^^^ ^^^ ^^v ^^^ ^^^ ^^^ ^^^

-22*         -12*         -2*
Tuyet's H3  ACC GTG TGC TAT GGC CTC ATG CT (SEQ ID NO:10)
             720                 730
DOR-1       ACg GTG TGC TAT GGC CTC ATG C> (SEQ ID NO:11)
[ 478 ]     ^^v ^^^ ^^^ ^^^ ^^^ ^^^ ^^^ ^
```

FIG.8a

```
         10             20             30            40
CCT GGC CTT TTG GGG ATG TGC TGT GCA AGA TAG TAA TTT CCA TTG
     50             60             70            80            90
ATT ACT ACA ACA TGT TCA CCA GCA TCT TCA CCT TGA CCA TGA TGA
         100            110            120           130
GCG TGG ACC GCT ACA TTG CCG TGT GCC ACC CCG TGA AGG CTT TGG
     140            150            160           170           180
ACT TCC GCA CAC CCT TGA AGG CAA AGA TCA TCA ATA TCT GCA TCT
         190            200            210           220
GGC TGC TGT CGT CAT CTG TTG GCA TCT CTG CAA TAG TCC TTG GAG
     230            240            250           260           270
GCA CCA AAG TCA GGG AAG GTA AGA GCA GTC ATT TCA TTC TGT TCA
         280            290            300           310
TAA AAA TGT AGC TTC AAA TTA CAT AGA CTT TTA ATT TGA GCG TGA
     320            330            340           350           360
GTA GGC CAC ATA TTT GTG GAA ATC GAT GCC AAA AGA CGA CGG AAA
         370            380            390           400
TGT AGT GCC TAA ATC CAT GGA AGA TGA GAA GTA GAA CAA TTT TTT
     410            420            430           440           450
GTC CCT TTC CAC CTC TAA ACA CAG AAT GCA ATA ATG ACA TTG CCA
         460            470            480           490
GAA GAG AGA TGC CCG ACC TGT CTC CCA TTC TGG CAA TGT TTA GTA
     500            510            520           530           540
GAA AGT GGA GGG GTG AGG ATG AGG TAA GAA CCA CAG GCA TGT AGA
         550            560            570           580
TTT TAA AGT ACA ACC TGG CAA GTC CAG ACA CAC CTT CTC ACT CCT
     590            600            610           620           630
TTT TTT CTC TTT AAC AAG GGA TAT AAA TTA TTG GTG ACA TAT GCT
         640            650            660           670
GGT TGT TTC CTC TTT TAT TCC TAA AGG ATA ACC TCC AAA TCA CTA
```

FIG.8b-1

```
       680         690         700         710         720
TTT TAA CAG CTT TGG CGT AGG ATC TCA AAA TCA AGT TAA CGG ATG
           730         740         750         760
    GTA GTT ACA GAT GAG TCA GAA CCA CTT GAT TTG GAC ATA TCA GGT
       770         780         790         800         810
TTT CCC TTG CAA ACC AGC CAA CTG ATT TTT TTT TTT TTT TTT TTT
           820         830         840         850
    GAG AGA GAG TCT TGC TCT GTT GCC AGG CTA GAG TGC AGT GGC GCG
       860         870         880         890         900
ATA TCG GCT CAC TGC AAC CTC TGC CTC CCG GGT TCA ACC TCA GCC
           910         920         930         940
    TCT CGA GTA GCT GGG ACT ACT GGC ACA CAC CAC CAT GCC CAG CTA
       950         960         970         980         990
ATT TTT GTA TTT TTA GTA GAG ACA GGG TTT CAC CGT GTT GGC CAG
          1000        1010        1020        1030
    GGT GGT CTC AAT CTC TTG ACC TCG TGA TCT GCC CGC CTC GNC TCC
      1040        1050        1060        1070        1080
CCA AAG TGC TGG GAT TAC AGG CGT GCN CTG CNC CCG NCC CCT GTT
          1090        1100        1110        1120
    GAT GTT TTT CCT GTA TTT CTA GGA CAG TAG TTC TCA CTC TGG GCT
      1130        1140        1150        1160        1170
GCA CAT TGG AAT CAC CTG GGT ACT TTA GAA AAC ACT GCT GCC TGC
          1180        1190        1200        1210
    ATC CCA CCC CTT AAG GGT CTG GTG TAA TTG ACC TGG GGT ACA GCC
      1220        1230        1240        1250        1260
TGG GTG TCA AGA TTT TTG AGC TCT CTC CAG GTG ACT CTG ACC TGC
          1270        1280        1290        1300
    AGC CAA GGT GAG AGG TAC TGT TCT AGG AGT TTT GCT TTA CTA GCA
      1310        1320        1330        1340        1350
AAA TAT AAA GCT ATA GAA AGC ATC TTT TGT TCC TCA TAG AAA TTA
```

FIG.8b-2

```
                1360           1370           1380           1390
ATG ATG GGG AGG TGA GCA GAA TAG TCA CTC TGG GCC TAC TCA TGC
        1400           1410           1420           1430           1440
TGT TTA ATG CTC CAG CAG GTA TAT AGG TTC TCC AGT TAC TAG GGG
                1450           1460           1470           1480
GTT CAT AAT ACC TGT GAG AGC AGA TAA CTG AGT GTA TAT AGT GAG
        1490           1500           1510           1520           1530
GAT TTC CAG GTC ATA GTG AAA GGG CAA GGC ACT AAA ATC ATA GCT
                1540           1550           1560           1570
TGT CTT GCA TAT ACT GTT TGT TTG TTT TTA GAC TTA CAT GTT AGG
        1580           1590           1600           1610           1620
TTT CAG TTT ACG TTT TAG GTT CAC AGC AAA ACT GAC CAG AAA GCA
                1630           1640           1650           1660
CAG AGA GGC ACT TCN ATT TAC CTC CAT TTA CCC CAC ACA GGC ACA
        1670           1680           1690           1700           1710
TCC TCC CCT ACA GAG TGG TCC ATT TAT TAC AGC TGC TGA ACC CAC
                1720           1730           1740           1750
ACT GAC ACG CTG TTA TCA CTC AGA GCC TGG CAG TTT ACA GAG GCT
        1760           1770           1780           1790           1800
CAC TCT CCG NTA TGT GTC CTG TGN TTT GAA CAA ATG TAT AAT GAC
                1810           1820           1830           1840
TTT ATT CAT TGT TTT TTA ATG AAG CTG ATC TTT TCC CTC TGA AAC
        1850           1860           1870           1880           1890
TAC AAA ATG AAT TTC TAG CAT AGC CAT AGC AGG TGT CAA GCT ATA
                1900           1910           1920           1930
CTA CTA GGT AAA TTT TAA GAA ATG CCC AAC TTT ATC ATA TTT GCA
        1940           1950           1960           1970           1980
TTT CAA AAT ATG ATT AAT CAC ACA TAG GAT TTT GTT TCT TCA TGC
                1990           2000           2010           2020
CTA CAG CAA ATA GAA ATA AAG TGC AAG AAA CTT TTC TGA GGC AAA
```

FIG.8b-3

```
           2030          2040          2050          2060          2070
            *             *             *             *             *
GCT TTC ACT TTG TGA ACG TAA AAT GTT GAC TCT AAT ATT TTC CAT
                 2080          2090          2100          2110
                  *             *             *             *
ACT GTA GTA TAT GTG TGT GTA TTA TGT GAG GAT TCA TAG TCT GCT
    2120          2130          2140          2150          2160
     *             *             *             *             *
CTT ACT TTT TTA TAG TAG CTA AGA ATT ATT ATA ATC GCT ATA AGC
                 2170          2180          2190          2200
                  *             *             *             *
AGA AAC AAT TAT TCT TAA CAA AAT GAA TAC ACA CAA GAA AAG CTT
    2210          2220          2230          2240          2250
     *             *             *             *             *
TAG TTT AGC TAT TAG AAC TAA CTC TAT AAT TAT GAT AAC CAT GAG
                 2260          2270          2280          2290
                  *             *             *             *
ATG CTG GAA CAG GAG CCA GCA GAA GCC ACA GCC CTC TGA TAT TAA
    2300          2310          2320          2330          2340
     *             *             *             *             *
TAT ATA AAG AAA CCA AAA TCT GCT TGT TAA ACT GAG GCA GTT GTA
                 2350          2360          2370          2380
                  *             *             *             *
TGG ATA CTT CAA CCT GAA AAT GCC CCC TTC TTC CTG AAA CAG AAC
    2390          2400          2410          2420          2430
     *             *             *             *             *
ATT TAA TAA AAA TGG CAT GCT TGG ACA GGA ATT TCT TTT TTA AAA
                 2440
                  *
AAT GCT TAG TTT TTA TG (SEQ ID NO:12)
```

FIG. 8b-4

```
          10                  20                  30                  40
           *                   *                   *                   *
TTC CTT TAT CTC CTA GAT ACA CCA AGA TGA AGA CTG CCA CCA ACA
     50                  60                  70                  80                  90
      *                   *                   *                   *                   *
TCT ACA TTT TCA ACC TTG CTC TGC AGA TGC CTT AGC CAC CAG TAC
          100                 110                 120                 130
            *                   *                   *                   *
CCT GCC CTT CCA GAG TGT GAA TTA CCT AAT GGG AAC ATG GCC ATT
          140                 150                 160                 170                 180
            *                   *                   *                   *                   *
TGG AAC CAT CCT TTG CAA GAT AGT GAT CTC CAT AGA TTA CTA TAA
          190                 200                 210                 220
            *                   *                   *                   *
CAT GTT CAC CAG CAT ATT CAC CCT CTG CAC CAT GAG TGT TGA TCG
     230                 240                 250                 260                 270
      *                   *                   *                   *                   *
ATA CAT TGC AGT CTG CCA CCC TGT CAA GGC CTT AGA TTT CCG TAC
          280                 290                 300                 310
            *                   *                   *                   *
TCC CNN NNN NNN NNN NNN NNN NNN NNN NNN NNN NNN NNN NNN NNN
     320                 330                 340                 350                 360
      *                   *                   *                   *                   *
NNN NNN NNN NNN NNN NNN NNN NNN NNN NNN NNN NNN NNN NNN NNN
          370                 380                 390                 400
            *                   *                   *                   *
NNN NNN NNG TTC CAT AGA TTG TAC ACT AAC ATT CTC TCA TCC AAC
     410                 420                 430                 440                 450
      *                   *                   *                   *                   *
CTG GTA CTG GGA AAA CCT GCT GAA GAT CTG TGT TTT CAT CTT CGC
```

FIG.8c-1

```
            460         470         480         490
             *           *           *           *
CTT CAT TAT GCC AGT GCT CAT CAT TAC CGT GTG CTA TGG ACT GAT
     500         510         520         530         540
      *           *           *           *           *
GAT CTT GCG CCT CAA GAG TGT CCG CAT GCT CTC TGG CTC CAA AGA
            550         560         570         580
             *           *           *           *
AAA GGA CAG GAA TCT TCG AAG GAT CAC CAG GAT GGT GCT GGT GGT
     590         600         610         620         630
      *           *           *           *           *
GGT GGC TGT GTT CAT CGT CTG CTG GAC TCC CAT TCA CAT TTA CGT
            640         650         660         670
             *           *           *           *
CAT CAT TAA AGC CTT GGT TAC AAT CCC AGA AAC TAC GTT CCA GAC
     680         690         700         710         720
      *           *           *           *           *
TGT TTC TTG GCA CTT CTG CAT TGC TCT AGG TTA CAC AAA CAG CTG
            730         740         750         760
             *           *           *           *
CCT CAA CCC AGT CCT TTA TGC ATT TCT GGA TGA AAA CTT AAA CGA
     770         780         790         800         810
      *           *           *           *           *
TGC TTC AGA GAG TTC TGT ATC CCA ACC TCT TCC AAC ATT GAG CAA
            820         830
             *           *
CAA AAC TCC ACT CGA ATT CC  (SEQ ID NO:13)
```

FIG.8c-2

```
         10            20            30            40
          *             *             *             *
GGG TAC CGG GCC CCC CCT CGA GGT CGA CGG TAT CGA TAA GCT TGA
   50            60            70            80            90
    *             *             *             *             *
TAT CGA ATT CTT ACT GAA TTA GGT ATC TTT CTT CAC ACT ACT TGG
         100           110           120           130
          *             *             *             *
TAA AAA AAA TGA AAA GGC AGA AAA ATT AGC CCC AAA AGA GAT GAA
   140           150           160           170           180
    *             *             *             *             *
ACT CTT CCG TCC ATC ACC ATT GAC TCT ATT GTG AAC TTA TGA AAA
         190           200           210           220
          *             *             *             *
AGG TAG TTG AGC AAT ATG AAG GCC ATG ATG TGG AAT TAA ACA CAC
   230           240           250           260           270
    *             *             *             *             *
ACA CAC ACA CAC ACA CAC ACA CAC ACA CAT GCT GGA TTC TAA ATG
         280           290           300           310
          *             *             *             *
TGT CCT TCC TCC TCT CAC TCT CTT GAT TCA AGT TTA TTT CTG AAC
   320           330
    *             *
TGA GAC ACG ATC ACC AC  (SEQ ID NO:14)
```

FIG.8d

```
         10           20           30           40
          *            *            *            *
CGG ATC CTT AGC ATC CCC AAA GCG CCT CCG TGT ACT TCT AAG GTG
         50           60           70           80           90
          *            *            *            *            *
GGA GGG GGA TAC AAG CAG AGG AGA ATA TCG GAC GCT CAG ACG TTC
        100          110          120          130
          *            *            *            *
CAT TCT GCC TGC CGC TCT TCT CTG GTT CCA CTA GGG CTT GTC CTT
        140          150          160          170          180
          *            *            *            *            *
GTA AGA AAC TGA CGG AGC CTA GGG CAG CTG TGA GAG GAA GAG GCT
        190          200          210          220
          *            *            *            *
GGG GCG CCT GGA ACC CGA ACA CTC TTG AGT GCT CTC AGT TAC AGN
        230          240          250          260          270
          *            *            *            *            *
CTA CCG AGT CCG CAG GAA GCA TTC AGA ACC ATG GAC AGC AGC GCC
        280          290          300          310
          *            *            *            *
GGC CCA GGG AAC ATC AGC GAC TGC TCT GAC CCC TTA GCT CCT GCA
        320          330          340          350          360
          *            *            *            *            *
AGT TGC TCC CCA GCA CCT GGC TCC TGG CTC AAC TTG TCC CAC GTT
        370          380          390          400
          *            *            *            *
GAT GGA AAC CAG TCC GAC CCA TGC GGT CCT AAC CCG ACG GGC CTT
        410          420          430          440          450
          *            *            *            *            *
GGC GGG AAC GAC AGC CTG TGC CCT CAG ACC GGC AGC CCT TCC ATG
        460          470          480          490
          *            *            *            *
GTC ACA GCC ATC ACC ATC ATG GCC CTC TAT TCT ATC GTG TGT GTA
        500          510          520          530          540
          *            *            *            *            *
GTG GGC CTC TTT GGA AAC TTC CTG GTC ATG TAT GTG ATT GTA AGA
        550          560          570          580
          *            *            *            *
TAT ACC AAA ATG AAG ACT GCC ACC AAC ATC TAC ATT TTC AAC CTT
        590          600          610          620          630
          *            *            *            *            *
GCT CTG GCA GAT GCC TTA GCC ACT AGC ACG CTG CCC TTT CAG AGT
        640          650          660          670
          *            *            *            *
GTT AAC TAC CTG ATG GGA ACG TGG CCC TTT GGA AAC ATC CTC TGC
```

FIG.9a

```
       680         690         700         710         720
        *           *           *           *           *
AAG ATC GTG ATC TCA ATA GAC TAC TAC AAC ATG TTC ACC AGT ATC
           730         740         750         760
            *           *           *           *
TTC ACC CTC TGC ACC ATG AGT GTA GAC CGC TAC ATT GCC GTC TGC
       770         780         790         800         810
        *           *           *           *           *
CAC CCG GTC AAG GCC CTG GAT TTC CGT ACC CCC CGA AAT GCC AAA
           820         830         840         850
            *           *           *           *
ATT GTC AAT GTC TGC AAC TGG ATC CTC TCT TCT GCC ATT GGT CTG
       860         870         880         890         900
        *           *           *           *           *
CCC GTA ATG TTC ATG GCA ACC ACA AAA TAC AGG CAG GGG TCC ATA
           910         920         930         940
            *           *           *           *
GAT TGC ACC CTC ACG TTC TCT CAT CCC ACA TGG TAC TGG GAG AAC
       950         960         970         980         990
        *           *           *           *           *
CTG CTC AAA ATC TGT GTC TTC ATC TTC GCC TTC ATC ATG CCG GGC
          1000        1010        1020        1030
            *           *           *           *
CTC ATC ATC ACT GTG TGT TAT GGA CTG ATG ATC TTA CAG CTC AAG
       1040        1050        1060        1070        1080
        *           *           *           *           *
AGT GTC CGC ATG CTG TCG GGC TCC AAA GAA AAG GAC AGG AAC CTG
          1090        1100        1110        1120
            *           *           *           *
CGC AGG ATC ACC CGG ATG GTG CTG GTG GTC GTG GCT GTA TTT ATT
       1130        1140        1150        1160        1170
        *           *           *           *           *
GTC TGC TGG ACC CCC ATC CAC ATC TAT GTC ATC ATC AAA GCA CTG
          1180        1190        1200        1210
            *           *           *           *
ATC ACG ATT CCA GAA ACC ACT TTC CAG ACT GTT TCC TGG CAC TTC
       1220        1230        1240        1250        1260
        *           *           *           *           *
TGC ATT GCC TTG GGT TAC ACA AAC AGC TGC CTG AAC CCA GTT CTT
          1270        1280        1290        1300
            *           *           *           *
TAT GCG TTC CTG GAT GAA AAC TTC AAA CGA TGT TTT AGA GAG TTC
       1310        1320        1330        1340        1350
        *           *           *           *           *
TGC ATC CCA ACT TCC TCC ACA ATC GAA CAG CAA AAC TCT GCT CGA
```

FIG.9b

```
      1360          1370          1380          1390
       *             *             *             *
ATC CGT CAA AAC ACT AGG GAA CAC CCC TCC ACG GCT AAT ACA GTG
    1400          1410          1420          1430          1440
     *             *             *             *             *
GAT CGA ACT AAC CAC CAG CTA GAA AAT CTG GAA GCA GAA ACT GCT
      1450          1460          1470          1480
       *             *             *             *
CCA TTG CCC TAA CTG GGT CCC ACG CCA TCC AGA CCC TCG CTA AAC
    1490          1500          1510          1520          1530
     *             *             *             *             *
TTA GAG GCT GCC ATC TAC TTG GAA TCA GGT TGC TGT CAG GGT TTG
      1540          1550          1560          1570
       *             *             *             *
TGG GAG GCT CTG GTT TCC TGG AAA AGC ATC TGA TCC TGC ATC ATT
    1580          1590          1600          1610          1620
     *             *             *             *             *
CAA AGT CAT TCC TCT CTG GCT ATT CAC GCT ACA CGT CAG AGA CAC
      1630          1640          1650          1660
       *             *             *             *
TCA GAC TGT GTC AAG CAC TCA GAA GGA AGA GAC TGC AGG CCA CTA
      1670          1680          1690          1700          1710
       *             *             *             *             *
CTG AAT CCA GCT CAT GTA CAG AAA CAT CCA ATG GAC CAC AAT ACT
      1720          1730          1740          1750
       *             *             *             *
CTG TGG TAT GTG ATT TGT GAT CAA CAT AGA AGG TGA CCC TTC CCT
    1760          1770          1780          1790          1800
     *             *             *             *             *
ATG TGG AAT TTT TAA TTT CAA GGA AAT ACT TAT GAT CTC ATC AAG
      1810          1820          1830          1840
       *             *             *             *
GGA AAA ATA GAT GTC ACT TGT TAA ATT CAC TGT AGT GAT GCA TAA
    1850          1860          1870          1880          1890
     *             *             *             *             *
AGG AAA AGC TAC CTC TGA CCT CTA GCC CAG TCA CCC TCT ATG AAA
      1900          1910          1920          1930
       *             *             *             *
AGT TCC ATA GGG AAT ATG TGA GGG AAA ATG TTG CTT CCA AAT AAA
    1940          1950          1960          1970          1980
     *             *             *             *             *
ATT TTC ACC TTT ATG TTA TAG TCT AGT TAA GAC ATC AGG GGC ATC
T (SEQ ID NO:15)
```

FIG.9c

HIGH HOMOLOGY BETWEEN DELTA, MU AND KAPPA OPIOD RECEPTORS

```
                              10        20        30        40        50
                              *         *         *         *         *
DOR-1                                      MELVPSARAELQSSPLVNLSDAFPSAFPSAGANASGSPGARSASSLALAI
              10        20        30        40        50        60
rMORa         mdsstgpgntsdcsdplaqascspapgswlnlShvdgNqSDpcglnrtglGgNdSlcPqt-gspSmvtAl>
                        10        20        30        40        50        60
rKORa                   mespiqifrgdpgptcspsacllpnsssswfpnwaesdsngsvgsedqqlesahiSpAipv>

60        70        80        90       100       110       120
            *         *         *         *         *         *         *
DOR-1       AITALYSAVCAVGLLGNVLVLVMFGIVRYTKLKTATNIYIFNLALADALATSTLPFQSAKYLMETWPFGELL
       70        80        90       100       110       120       130
rMORa  tlmALYSiVCvVGLfGNfLVMvvIVRYTKmKTATNIYIFNLALADALATSTLPFQSvnYLMgTWPFGtiL>
       70        80        90       100       110       120       130
rKORa  iITAvYSvvFvVGLvGNsLVMFviiRYTKmKTATNIYIFNLALADALvTtTmPFQSAvYLMnsWPFGdvL>

130       140       150       160       170       180       190
            *         *         *         *         *         *         *
DOR-1       CKAVLSIDYYNMFTSIFTLTMMSVDRYIAVCHPVKALDFRTPAKAKLINICIWVLASGVGVPIMVAVTQ
        140       150       160       170       180       190       200
rMORa   CKiViSIDYYNMFTSIFTLctMSVDRYIAVCHPVKALDFRTPrnAKivNvCnWiLSSaiGlPvMfMAttK>
        140       150       160       170       180       190       200
rKORa   CKiViSIDYYNMFTSIFTLTMMSVDRYIAVCHPVKAKLDFRTPiKAKiINICIWiLASSVGisaiVlggTk>
```

```
              200       210       220       230       240       250       260
               *         *         *         *         *         *         *
DOR-1         PRDGAVVCMLQFPSPSWYWDTVTKICVFLFAFVVPILIITVCYGLMLLRSVRLLSGSKEKDRSLRRIT
              210       220       230       240       250       260       270
               *         *         *         *         *         *         *
rMORa         yRqGsidCtLtFshPtWYwenllKICVFiFAFimPILIITVCYGLMiLRLKSVRmLSGSKEKDRnLRRIT>
                   vd
                      |210       220       230       240       250       260       270
                   ys  *         *         *         *         *         *         *
rKORa         vRedvieCsLQFPddeW-WDIfmKICVFvFAFViPvLIIiVCYtLMiLRLKSVRLLSGSrEKDRnLRRIT>

270       280       290       300       310       320       330
               *         *         *         *         *         *         *
DOR-1         RMVLVVVGAFVVCWAPIHIFVIVWTLVDINRRDPLVVAALHLCIALGYANSSLNPVLYAFLDENFKRCFR
              280       290       300       310       320       330       340
               *         *         *         *         *         *         *
rMORa         RMVLVVVavFIVCWtPIHIyVIikaLitI-pettfgtvsWHfCIALGYtNScLNPVLYAFLDENFKRCFR>
                    280       290       300       310       320       330       340
                     *         *         *         *         *         *         *
rKORa         klVLVVVavFiiCWtPIHIFilVealgstshsta-alssyyfCIALGYtNSSLNPVLYAFLDENFKRCFR>

340       350       360       370
               *         *         *         *
DOR-1         QLCRTPCGRQEPGSLRRPRQATTRERVTACTPSDGPGGGAAA (SEQ ID NO:8)
              350       360       370       380
               *         *         *         *
rMORa         efCiptsstiEqanstRvRQ-nTREhpstantvDrtnhqlenleaetaplp(SEQ ID NO:16)
                    350       360
                     *         *
rKORa         dfCfpikmRmEraStnRvRn-Tvqdpasmrdvggmnkpv> (SEQ ID NO:17)
```

Identical amino acids between DOR-1 and mu and kappa receptors in upper case Predicted transmembrane domains are underlined

```
                 *              *              *              *            54
GGC AGT GGC ATG GAG CCC CTC TTC CCC GCG CCG TTC TGG GAG GTT ATC TAC GGC
                                                                         108
         *              *              *              *             *
AGC CAC CTT CAG GGC AAC CTG TCC CTC CTG AGC CCC AAC CAC AGT CTG CTG CCC
                                                                         162
  *              *              *              *              *       *
CCG CAT CTG CTG CTC AAT GCC AGC CAC GGC GCC TTC CTG CCC CTC GGG CTC AAG
                                                                         216
         *              *              *              *             *
GTC ACC ATC GTG GGG CTC TAC CTG GCC GTG TGT GTC GGA GGG CTC CTG GGG AAC
                                                                         270
  *              *              *              *              *       *
TGC CTT GTC ATG TAC GTC ATC CTC AGG CAC ACC AAA ATG AAG ACA GCC ACC AAT
                                                                         324
         *              *              *              *             *
ATT TAC ATC TTT AAC CTG GCC CTG GCC GAC ACT CTG GTC CTG CTG ACG CTG CCC
                                                                         378
  *              *              *              *              *       *
TTC CAG GGC ACG GAC ATC CTC CTG GGC TTC TGG CCG TTT GGG AAT GCG CTG TGC
                                                                         432
  *              *              *              *              *       *
AAG ACA GTC ATT GCC ATT GAC TAC TAC AAC ATG TTC ACC AGC ACC TTC ACC CTA
                                                                         486
         *              *              *              *             *
ACT GCC ATG AGT GTG GAT CGC TAT GTA GCC ATC TGC CAC CCC ATC CGT GCC CTC
                                                                         540
  *              *              *              *              *       *
GAC GTC CGC ACG TCC AGC AAA GCC CAG GCT GTC AAT GTG GCC ATC TGG GCC CTG
                                                                         594
         *              *              *              *             *
GCC TCT GTT GTC GGT GTT CCC GTT GCC ATC ATG GGC TCG GCA CAG GTC GAG GAT
                                                                         648
         *              *              *              *             *
GAA GAG ATC GAG TGC CTG GTG GAG ATC CCT ACC CCT CAG GAT TAC TGG GGC CCG
                                                                         702
  *              *              *              *              *       *
GTG TTT GCC ATC TGC ATC TTC CTC TTC TCC TTC ATC GTC CCC GTG CTC GTC ATC
                                                                         756
         *              *              *              *             *
TCT GTC TGC TAC AGC CTC ATG ATC CGG CGG CTC CGT GGA GTC GCC CTG CTC TCG
                                                                         810
  *              *              *              *              *       *
GGC TCC CGA GAG AAG GAC CGG AAC CTG CGG CGC ATC ACT CGG CTG GTG CTG GTG
```

*FIG. 11A*

```
                *           *           *           *           *    864
GTA GTG GCT GTG TTC GTG GGC TGC TGG ACG CCT GTC CAG GTC TTC GTG CTG GCC
                *           *           *           *           *    918
CAA GGG CTG GGG GTT CAG CCG AGC AGC GAG ACT GCC GTG GCC ATT CTG CGC TTC
                *           *           *           *           *    972
TGC ACG GCC CTG GGC TAC GTC AAC AGC TGC CTC AAC CCC ATC CTC TAC GCC TTC
                *           *           *           *           *    1026
CTG GAT GAG AAC TTC AAG GCC TGC TTC CGC AAG TTC TGC TGT GCA TCT GCC CTG
                *           *           *           *           *    1080
CGC CGG GAC GTG CAG GTG TCT GAC CGC GTG CGC AGC ATT GCC AAG GAC GTG GCC
                *           *           *           *           *    1134
CTG GCC TGC AAG ACC TCT GAG ACG GTA CCG CGG CCC GCA TGA CTA GGC GTG GAC
                *           *           *           *           *    1188
CTG CCC ATG GTG CCT GTC AGC CCG CAG AGC CCA TCT ACG CCC AAC ACA GAG CTC
                *           *           *           *           *    1242
ACA CAG GTC ACT GCT CTC TAG GCG GAC ACA CCC TGG GCC CTG AGC ATC CAG AGC
                *           *           *           *           *    1296
CTG GGA TGG GCT TTT CCC TGT GGG CCA GGG ATG CTC GGT CCC AGA GGA GGA CCT
                *           *           *           *           *    1350
AGT GAC ATC ATG GGA CAG GTC AAA GCA TTA GGG CCA CCT CCA TGG CCC CAG ACA
                *           *           *           *           *    1404
GAC TAA AGC TGC CCT CCT GGT GCA GGG CCG AGG GGA CAC AAG GAC CTA CCT GGA
                *           *           *           *           *    1458
AGC AGC TGA CAT GCT GGT GGA CGG CCG TTA CTG GAG CCC GTG CCC CTC CCT CCC
                *           *           *           *           *    1512
CGT GCT TCA TGT GAC TCT TGG CCT CTC TGC TGC TGC GTT GGC AGA ACC CTG GGT
                *           *           *           *           *    1566
GGG CAG GCA CCC GGA GGA GGA GCA GCA GCT GTG TCA TCC TGT GCC CCC CAT GTG
                *           *           *           *           *    1620
CTG TGT GCT GTT TGC ATG GCA GGG CTC CAG CTG CCT TCA GCC CTG TGA CGT CTC
                *           *           *           *           *    1674
```

*FIG. 11B*

```
CTC AGG GCA GCT GGA CAG GCT TGG CAC GGC CCG GGA AGT GCA GCA GGC AGC TTT
                                                                    1728
      *           *           *           *           *
TCT TTG GGG TGG GAC TTG CCC TGA GCT TGG AGC TGC CAC CTG GAG GAC TTG CCT
                                                                    1782
  *           *           *           *           *           *
GTT CCG ACT CCA CCT GTG CAG CCG GGG CCA CCC CAG GAG AAA GTG TCC AGG TGG
          *           *
GGG CTG GCA GTC CCT GGC TGC AG  (SEQ ID NO:18)
```

FIG. 11C

```
                   10        20        30        40        50        60
hMOR       MDSSAAPTYASYCTDALAYSSCSPAPSPGSWVYLSHLDGYLSDPCGPYRTNLGGRDSLCPPTGSP
                                                                        tg
hDOR                         mePAPSaGoelq-pplfaYaSDaypsacpsaGaYaSgpParsas
mKOR                  mespiqifrgdpgptcspSaC-llPVssSWfp-nwaesdsYgsvGsedqqLes-ahi-sP-aiP
                                                    tev                      tf
ORL1                         meplfPaP-PWiygSHLqGYLSll-sPYhslLpphllLYashGal
ORL2                                        meeggdfdnyygadYqSeCeyTdwk

*70******80****90** 100     110********120        130
hMOR       SMITAITIMALYSIVCVVGLFGNFLYMYVIVRYTKMKTATNIYIFNLALADALATSTLPFQSVNY
hDOR       SlalAIaItALYSaVCaVGlGNsLVMfgIVRYTKMKTATNIYIFNLALADALATSTLPFQSakY
mKOR       -vI--IT--AvYSvVPVVGLvGNsLYMfVIiRYTKMKTATNIYIFNLALADLvTtTmPFQSavY
ORL1       plglkvTIvglYlaVCVgGLlGNclVMYVIlRhTKMKTATNIYIFNLALADtLvllTLPFQgtdi
                                                                  te     tw
ORL2       S-sgAL-IpAiYmlVFllGttGNgLVlwtvfRssrkrrsodIFIasLAvADltfvvTLPlatytY 140     *150***160* 170       180       190***
hMOR       LMGTWPFGTILCKIVISIDYYNMFTSIFTLCTWSVDRYIAVCHPVKALDFRIPRNAKIINVCNWI
hDOR       LMeTWPFGelLCKaVISIDYYNMFTSIFTLtmMSVDRYIAVCHPVKALDFRTPakAKlINiClWv
mKOR       LMnsWPFGdvLCKIVISIDYYNMFTSIFTLtmMSVDRYIAVCHPVKALDFRTPlkAKIINiCiWl
ORL1       LIGPWPFGnaLCKtVIaIDYYNWFTStFTLtaMSVDRYvAiCHPirALDvRTsskAqavNVaiWa
ORL2       rdydWPFGTffCKlssylifvNMyaSvvFcltglSFDRYlAivrPVanarlRlrvsgavatavlWv

200***210       220       230    240*****250*****260
hMOR       LSSAIGLPVMFMATTKYRQGSIDCTLTFSHPTWYWENLVKICVFIFAFIMPVLIITVCYGLMILR
hDOR       LaSgvGvPiMVMAvTrpRdGavvCmLqFpsPsWYWdtvtKICVFlFAFvvPiLIITVCYGLMlLR
                                  tdv              tys
mKOR       LaSsvGisaivlggTKvRedvIeCsLqFpddeW-WdlfmKICVFvFAFviPVLIIiVCYtLMILR
hORL1      LaSvvGvPVaiMgsaqvedeeIeClveiptPqdYWgpvfaICiFlFsFIvPVLvIsVCYsLMIrR
                           tr     tk           tmvatv
hORL2      LoallamPVMvitTgdlenttvqCymdySsseWaWEvglgvssttvgFvvPftImltCY-ffIaq
```

FIG. 12A

```
              270        280   *****290******300*     310   ***320 ****
hMOR    LKSVRMLSGSKEKDRMNLRRITRMVLVVVAVFIVCWTPIHIYVIIKALVTIPETTFQTVSWHFCIA
                                                                 td
hDOR    LrSVRILSGSKEKDRsLRRITRMVLVVVgaFvVCWoPIHIfVIvwtLVdIrrdplvvaaIHICIA
mKOR    LKSVRILSGSrEKDRNLRRITklVLVVVAVFIlCWTPIHIfilveALgstshsToolsSyyFCIA
ORL1    LrgVRILSGSrEKDRNLRRITRlVLVVVAVFvgCWTPvqvfVlaqgLgvqPssetavailrFCtA
                                                    tlvkt         tf
ORL2    tiaghfrkeriEglRkrRRllsiivVlVvtFalCWmPyHlYmlgslLhwpcdddlFlmnifpyCtc

330****340       350       360       370       380       390
hMOR    LGYTNSCLNPVLYAFLDENFKRCFREFCIPTSSNIEQQNSTRIRQNTTOMPSTANTVDRTNHQLE
hDOR    LGYaNSsLNPVLTAFLDENFKRCFRqlCrkpcgrpdpssfsRaReaTareryTActpsdgpggga
mKOR    LGYTNSsLMPVLTAFLDENFKARCFRdFCFPikmrmErQstnRvR-NTvqdPasmrdVggmnkpv
ORL1    LGYvNSCLMPiLYAFLDENFKaCFRkFCcasalirrdvQvSdRvRsiakDvalackTsetvprpa
                                                                       ↑
                                                          tq    (SEQ ID NO:23)
ORL2    isYvNSCLMPfLYAFfDprFraCtsmlCcgqSrcagtshSssgeksasyssghsqqpgprmgkgg
                                                                        ↑
                                                                  (SEQ ID NO:24)
            400.
hMOR    NLEAETAPLP  (SEQ ID NO:20)
h-DOR   aa  (SEQ ID NO:21)
ORL2    eqmheksipysqetlvvd  (SEQ ID NO:22)
```

*FIG. 12B*

METHODS OF SCREENING MODULATORS OF OPIOID RECEPTOR ACTIVITY

CROSS-REFERENCE TO RELATED APPLICATIONS

This application is a continuation-in-part of U.S. Ser. No. 08/403,260 filed Mar. 13, 1995, and now abandoned which is a continuation-in-part of U.S. Ser. No. 08/387,707 filed Feb. 13, 1995 and now U.S. Pat. No. 6,265,563 which is a national phase of PCT application US 93/07665 filed Aug. 13, 1993, which is a continuation-in-part of U.S. Ser. No. 07/929,200 filed Aug. 13, 1992 and now abandoned. The contents of these applications is incorporated herein by reference.

This invention was made with Government support under Grant No. DA05010 awarded by the Alcohol, Drug Abuse and Mental Health Administration. The Government has certain rights in the invention.

TECHNICAL FIELD

The invention relates to substances involved in vertebrate nervous systems, and in particular to the opioid receptors and receptor-like proteins (also referred to as opioid receptors herein) and activities mediated thereby. Accordingly, the invention concerns recombinant materials useful for the production of opioid receptors, the receptor as a diagnostic tool, therapeutic and diagnostic compositions relevant to the receptor, and methods of using the receptor to screen for drugs that modulate the activity of the receptor.

BACKGROUND ART

The term "opioid" generically refers to all drugs, natural and synthetic, that have morphine-like actions. Formerly, the term "opiate" was used to designate drugs derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources have continued to use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

A significant feature of the analgesia produced by opioids is that it occurs without loss of consciousness. When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

The development of tolerance and physical dependence with repeated use is a characteristic feature of all opioid drugs, and the possibility of developing psychological dependence on the effect of these drugs is a major limitation for their clinical use. There is evidence that phosphorylation may be associated with tolerance in selected cell populations (Louie, A. et al. *Biochem Biophys Res Comm* (1988) 152:1369–75).

Acute opioid poisoning may result from clinical overdosage, accidental overdosage, or attempted suicide. In a clinical setting, the triad of coma, pinpoint pupils, and depressed respiration suggest opioid poisoning. Mixed poisonings including agents such as barbiturates or alcohol may also contribute to the clinical picture of acute opioid poisoning. In any scenario of opioid poisoning, treatment must be administered promptly.

The opioids interact with what appear to be several closely related receptors. Various inferences have been drawn from data that have attempted to correlate pharmacologic effects with the interactions of opioids with a particular constellation of opioid receptors (Goodman and Gilman's, *THE PHARMACOLOGICAL BASIS OF THERAPEUTICS*, 7th ed, pp. 493–95 (MacMillan 1985)). For example, analgesia has been associated with mu and kappa receptors. Delta receptors are believed to be involved in alterations of affective behavior, based primarily on the localization of these receptors in limbic regions of the brain. Additionally, activation, e.g., ligand binding with stimulation of further receptor-mediated responses, of delta opioid receptors is believed to inhibit the release of other neurotransmitters. The pathways containing relatively high populations of delta opioid receptor are similar to the pathways implicated to be involved in Huntington's disease. Accordingly, it is postulated that Huntington's disease may correlate with some effect on delta opioid receptors.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., *Science* (1973) 179:1011–1014), the differential pharmacological and physiological effects of both opioid peptide analogues and alkaloid opiates served to delineate multiple opioid receptors. Accordingly, three anatomically and pharmacologically distinct opioid receptor types have been described: delta, kappa and mu. Furthermore, each type is believed to have sub-types (Wollemann, M., *J Neurochem* (1990) 54:1095–1101; Lord, J. A., et al., *Nature* (1977) 267:495–499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: *Biological Basis of Substance Abuse*, S. G. Korenman & J. D. Barchas, eds., Oxford University Press (in press); North, A. R., et al., *Proc Natl Acad Sci USA* (1990) 87:7025–29; Gross, R. A., et al., *Proc Natl Acad Sci USA* (1990) 87:7025–29; Sharma, S. K., et al., *Proc Natl Acad Sci USA* (1975) 72:3092–96). Although the functional mechanisms are the same, the behavioral manifestations of receptor-selective drugs differ greatly (Gilbert, P. E. & Martin, W. R., *J Pharmacol Exp Ther* (1976) 198:66–82).

Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., *Trends in Neurosci* (1988) 11:308–14). The rat cerebellum is remarkably devoid of opioid receptors including delta opioid receptors.

Several opioid molecules are known to selectively or preferentially bind delta receptors. Of the vertebrate endogenous opioids, the enkephalins, A particularly met-enkephalin (SEQ ID NO:1) and leu-enkephalin (SEQ ID NO:2), appear to possess the highest affinity for delta receptors, although the enkephalins also have high affinity for mu receptors. Additionally, the deltorphans, peptides isolated from frog skin, comprise a family of opioid peptides that have high affinity and selectivity for delta receptors (Erspamer, V., et al., *Proc Natl Acad Sci USA* (1989) 86:5188–92).

A number of synthetic enkephalin analogues are also delta receptor-selective including (D-Ser$^2$) leucine enkephalin Thr (DSLET) (SEQ ID NO:3) (Garcel, G. et al. *FEBS Lett* (1980) 118:245–247),and (D-Pen$^2$, D-Pen$^5$) enkephalin (DPDPE) (SEQ ID NO:4) (Akiyama, K. et al., *Proc Natl Acad Sci USA* (1985) 82:2543–2547).

Recently a number of other selective delta receptor ligands have been synthesized, and their bioactivities and binding characteristics suggest the existence of more than one delta receptor subtype (Takemori, A. E., et al., *Ann Rev Pharm Toxicol*, (1992) 32:239–69; Negri, L., et al., *Eur J Pharmacol* (1991) 196:355–335; Sofuoglu, M., et al., *Pharmacologist* (1990) 32:151).

Although the syntrhetic pentapeptide 2dAla, 5dLeu enkephalin (DADLE) (SEQ ID NO:5) was considered to be delta-selective, it also binds equally well to mu receptors. The synthetic peptide D-Ala$^2$-N-Me-Phe$^4$-Gly-ol$^5$-enkephalin (DAGO) (SEQ ID NO:6) has been found to be a selective ligand for mu-receptors.

The existence of multiple delta opioid receptors has been implied not only from the pharmacological studies addressed above, but also from molecular weight estimates obtained by use of irreversible affinity ligands. Molecular weights for the delta opioid receptor that range from 30 kDa to 60 kda (Evans, C. J., supra; Evans, C. J. et al., *Science* (1992) 258:1952–1955, which document corresponds to the disclosure of the priority document of the present application; Bochet, P. et al., *Mol Pharmacol* (1988) 34:436–43). The various receptor sizes may represent alternative splice products, although this has not been established.

Many studies of the delta opioid receptor have been performed with the neuroblastoma/glioma cell line NG108-15, which was generated by fusion of the rat glial cell line (C6BU-1) and the mouse neuroblastoma cell line (N18-TG2) (Klee, W. A. and Nirenberg, M. A., *Proc Natl Acad Sci USA* (1974) 71:3474–3477). The rat glial cell line expresses essentially no delta opioid receptors, whereas the mouse neuroblastoma cell line expresses low amounts of the receptor. Thus, it has been suggested that the delta receptor in the NG108-15 cells is of mouse chromosomal origin (Law, *Mol Pharm* (1982) 21:438–91). Each NG108-15 cell is estimated to express approximately 300,000 delta-receptors. Only delta-type opioid receptors are expressed, although it is not known whether these represent more than a single subtype. Thus, the NG108-15 cell line has served to provide considerable insight into the binding characterization of opioid receptors, particularly delta opioid receptors. However, the NG108-15 cell line is a cancer-hybrid and may not be completely representative of the delta receptor in endogenous neurons due to the unique cellular environment in the hybrid cells.

An extensive literature has argued that the opioid receptors are coupled to G-proteins (see, e.g., Schofield, P. R., et al., *ERBO J* (1989) 8:489–95), and are thus members of the family of G-protein coupled receptors. G-proteins are guanine nucleotide binding proteins that couple the extracellular signals received by cell surface receptors to various intracellular second messenger systems. Identified members of the G-protein-coupled family share a number of structural features, the most highly conserved being seven apparent membrane-spanning regions, which are highly homologous among the members of this family (Strosberg, A. D., *Eur J Biochem* (1991) 196:1–10). Evidence that the opioid receptors are members of this family includes the stimulation of GTPase activity by opioids, the observation that GTP analogues dramatically effect opioid and opiate agonist binding, and the observation that pertussis toxin (which by ADP ribosylation selectively inactivates both the Gi and Go subfamilies of G-proteins) blocks opioid receptor coupling to adenylate cyclase and to K$^+$ and Ca$^{2+}$ channels (Evans, C. J., supra).

The members of the G-protein-coupled receptor family exhibit a range of characteristics. Many of the G-protein-coupled receptors, e.g., the somatostatin receptor and the angiotensin receptor, have a single exon that encodes the entire protein coding region (Strosberg supra; Langord, K., et al., *Biochem Biophys Res Comm* (1992) 138:1025–1032). However, other receptors, such as substance P receptor and the dopamine D-2 receptor, contain the protein coding region. The D-2 receptor is particularly interesting in that alternate splicing of the gene gives rise to different transcribed products (i.e., receptors) (Evans, C. J., supra; Strosberg, supra). Interestingly, somatostatin ligands are reported to bind to opioid receptors (Terenius, L., *Eur J Pharmacol* (1976) 38:211; Mulder, A. H., et al., *Eur J Pharmacol* (1991) 205:1–6) and, furthermore, to have similar molecular mechanisms (Tsunoo, A., et al., *Proc Natl Acad Sci USA* (1986) 83:9832–9836).

In previous efforts to describe and purify opioid receptors, two clones have been described that were hypothesized either to encode a portion of or entire opioid receptors. The first clone, which encodes the opiate binding protein OBCAM (Schofield et al., supra), was obtained by utilizing a probe designed from an amino acid sequence of a protein purified on a morphine affinity column. OBCAM lacks any membrane spanning domains but does have a C-terminal domain that is characteristic of attachment of the protein to the membrane by a phosphatidylinositol (PI) linkage. This feature, which is shared by members of the immunoglobulin superfamily, is not common to the family of receptors coupled to G-proteins. Thus, it has been proposed that OBCAM is part of a receptor complex along with other components that are coupled to G-proteins (Schofield et al., supra). At present, however, there is no direct evidence for such a complex.

A second proposed opioid receptor clone was obtained in an effort to clone a receptor that binds kappa opioid receptor ligands (Xie, G. X., *Proc Natl Acad Sci USA* (1992) 89:4124–4128). A DNA molecule encoding a G-coupled receptor from a placental cDNA library was isolated. This receptor has an extremely high homology with the neurokinin B receptor (84% identical throughout the proposed protein sequence). When this clone was expressed in COS cells, it displayed opioid peptide displaceable binding of $^3$H-bremazocine (an opiate ligand with high affinity for kappa receptors). However, the low affinity of this receptor for $^3$H-bremazocine, and the lack of appropriate selectivity since this receptor (binding both mu and delta ligands) made it doubtful that this cloned molecule is actually an opioid receptor.

Furthermore, characterization of opioid receptor proteins has proven difficult because of their instability once solubilized from the membrane; purified delta opioid receptors have not been isolated. The previous estimates of opioid receptor molecular weights ranging from 30 kDa to 60 Kda further reflect the difficulty in isolating and characterizing these proteins.

Recently, DNA encoding the murine kappa and delta opioid receptors from mouse brain was reported by Yasuda, K. et al. *Proc Natl Acad Sci USA* (1993) 90:6736–6740. The sequence of the clones indicated the presence of the expected seven transmembrane regions. In addition, Chen, Y. et al. in a soon-to-be-published manuscript in *Molecular Pharmacology* (1993) report the "molecular cloning and functional expression of a mu opioid receptor from rat brain". In fact, the rat mu receptor was cloned using the present inventors' DOR-1 clone, which lends enabling support to the present invention disclosed below. The mouse delta opioid receptor was disclosed as having been cloned (Kieffer, B. J. et al., *Proc Natl Acad Sci USA* (1992) 89:12048–12052 (December issue) after the filing date of the priority document of the present application. However, the sequence reported therein differs from the sequence reported by the present inventors for the mouse delta receptor (Evans et al., 1992, supra; this disclosure).

In addition to the opioid receptors which respond to specified agonists, the delta, kappa and mu opioid receptors, additional forms of these proteins, commonly called opioid receptor-like (ORL) proteins have been obtained using the methods described herein. Using these methods, two human ORL protein-encoding cDNAs were obtained from a human brain stem cDNA library. One of these clones is equivalent to that isolated by O'Dowd, B. F. et al. *Gene* (1993) 136:355–360; the other, ORL-1, is identical to that reported by Mollereau, C. et al. *FEBS Lett* (1994) 341:33–38. A preliminary report of the present work appeared in *Regulatory Peptides* (1994) 54:143–144 and is incorporated herein by reference.

DISCLOSURE OF THE INVENTION

The present invention provides recombinant nucleic acid molecules which encode the murine delta opioid receptor, as well as recombinant nucleic acid molecules which can be retrieved using low-stringency hybridization to this disclosed DNA. Thus, the invention provides genes encoding the delta, kappa and mu receptors, representing opioid receptors generally, including ORL proteins, of any species containing genes encoding such receptors or ORL proteins sufficiently homologous to hybridize under low-stringency conditions described herein.

As used herein, "opioid receptors" includes not only the previously identified delta, kappa and mu receptors, but also additional receptor-like proteins, represented by, for example, ORL-1 that hybridize under the low-stringency conditions described to the murine DOR clone set forth herein, and which have opioid receptor characteristics including seven putative transmembrane regions, and ability to couple with guanine nucleotide-binding regulatory proteins (G proteins) to inhibit adenylyl cyclase and/or calcium channels or to stimulate potassium channels. Thus, when the word "opioid receptor" is used hereinbelow, this term is intended to include this entire genus.

Thus, in one aspect, the invention is directed to recombinant nucleic acid molecules and methods for the production of an opioid receptor wherein the opioid receptor is encoded by a gene which hybridizes under low-stringency to the nucleotide sequence of FIG. 5 or to its complement. By "low-stringency" is meant 50% formamide/6×SSC, overnight at 37° C. for the hybridization, followed by washes at 2×SSC 0.1% SDS at room temperature or 50% formamide/ 6×SSC at 37° C. with washes of 1×SSC/0.1% SDS at 37° C.

Also provided are expression systems comprising the nucleic acid molecules described above. The receptor can be recombinantly produced using these expression systems and host cells modified to contain them.

Especially useful are vertebrate cells which express the opioid receptor gene so that the opioid receptor protein is displayed at the surface of the cells. These cells offer means to screen native and synthetic candidate agonists and antagonists for the opioid receptors.

In still other aspects, the invention is directed to methods to screen candidate agonists and/or antagonists acting at opioid receptors using the recombinant transformed cells of the invention. Such assays include (1) binding assays using competition with ligands known to bind opioid receptors, (2) agonist assays which analyze activation of the secondary pathways associated with opioid receptor activation in the transformed cells, and (3) assays which evaluate the effect on binding of the candidate to the receptor by the presence or absence of sodium ion and GTP. Antagonist assays include the combination of the ability of the candidate to bind the receptor while failing to effect further activation, and, more importantly, competition with a known agonist.

Still another aspect of the invention is provision of antibody compositions which are immunoreactive with the opioid receptor proteins. Such antibodies are useful, for example, in purification of the receptors after solubilization or after recombinant production thereof.

In still other aspects, the invention is directed to probes useful for the identification of DNA which encodes related opioid receptors in various species or different types and subtypes of opioid receptors.

Accordingly, an object of the present invention is to provide an isolated and purified form of a DNA sequence encoding an opioid receptor, which is useful as a probe as well as in the production of the receptor.

Another object is to provide a recombinantly produced DNA sequence encoding an opioid receptor.

Another object is to produce an antisense sequences corresponding to known sense sequences encoding the opioid receptors.

Another object of the invention is to provide a DNA construct comprised of a control sequence operatively linked to a DNA sequence which encodes an opioid receptor and to provide recombinant host cells modified to contain the DNA construct.

Another object is to isolate, clone and characterize, from various vertebrate species, DNA sequences encoding the various related receptors, by hybridization of the DNA derived from such species with a native DNA sequence encoding the opioid receptor of the invention.

An advantage of the present invention is that opioid receptor-encoding DNA sequences can be expressed at the surface of host cells which can conveniently be used to screen drugs for their ability to interact with and/or bind to the receptors.

These and other objects, advantages and features of the present invention will become apparent to those persons skilled in the art.

BRIEF DESCRIPTION OF THE DRAWINGS

FIG. 5 shows the nucleotide sequence (SEQ ID NO:7) and the deduced amino acid sequence (SEQ ID NO:8) of the DOR-1 clone.

FIG. 6 the deduced amino acid sequence of DOR-1 (SEQ ID NO:8) compared with the rat somatostatin receptor. Consensus glycosylation sites predicted to fall in extracellular domains are indicated by an asterisk. Potential protein kinase C sites are listed in Example 5. The seven predicted membrane spanning regions (underlined) are predicted based on the hydrophobicity profile and published predictions (Macvector software program (IBI); T. Hopp, and K. Woods, *Proc Natl Acad Sci USA* (1981) 78:3842–3828). For sequencing, the cDNA insert was subcloned into pBluescript and both strands were sequenced from single-stranded DNA using Sequenase and Taq cycle sequencing. For ambiguities due to compressions 7-deaza-dGTP replaced dGTP in the sequencing reactions and the products were resolved on formamide gels.

FIG. 8a (SEQ ID NO:10 and SEQ ID NO:11) shows a partial nucleotid)e sequence of the human delta opioid receptor genomic clone H3 (also designated human DORa or hDORa).

FIG. 8b (SEQ ID NO:12) partial nucleotide sequence of the human kappa opioid receptor genomic clone H14 (also designated human KORa or hKORa).

FIG. 8c (SEQ ID NO:13) shows a partial nucleotide sequence of the human mu opioid receptor genomic clone H20 (also designated human MORa or hMORa), FIG. 8d (SEQ ID NO:14) shows the nucleotide sequence of the CACACA repeat near the H20 DNA.

FIG. 9 (SEQ ID NO:15) shows the nucleotide sequence of the murine mu-receptor clone DOR-2 also named mMOR-1 or mMOR-1α.

FIG. 10 (SEQ ID NO:8 and SEQ ID NO:16 and SEQ ID NO:17) shows the homology of various receptor amino acid sequences.

FIG. 11 (SEQ ID NO:18) shows the complete DNA sequence of the cDNA retrieved from a human brain stem cDNA library and comprising a nucleotide sequence encoding the opioid receptor ORL-1. This cDNA encodes a 370-amino acid opioid receptor protein (SEQ ID NO:19).

FIG. 12 (SEQ ID NO:20–SEQ ID NO:24) shows a comparison of ORL-1 and ORL-2 amino acid sequences with various human and murine delta, kappa, and mu receptors. ORL-1 is a protein of 370 amino acids and is compared with human mu opioid receptor (hMOR), human delta opioid receptor (hDOR) and murine kappa opioid receptor (mKOR).

MODES OF CARRYING OUT THE INVENTION

Figure 1:
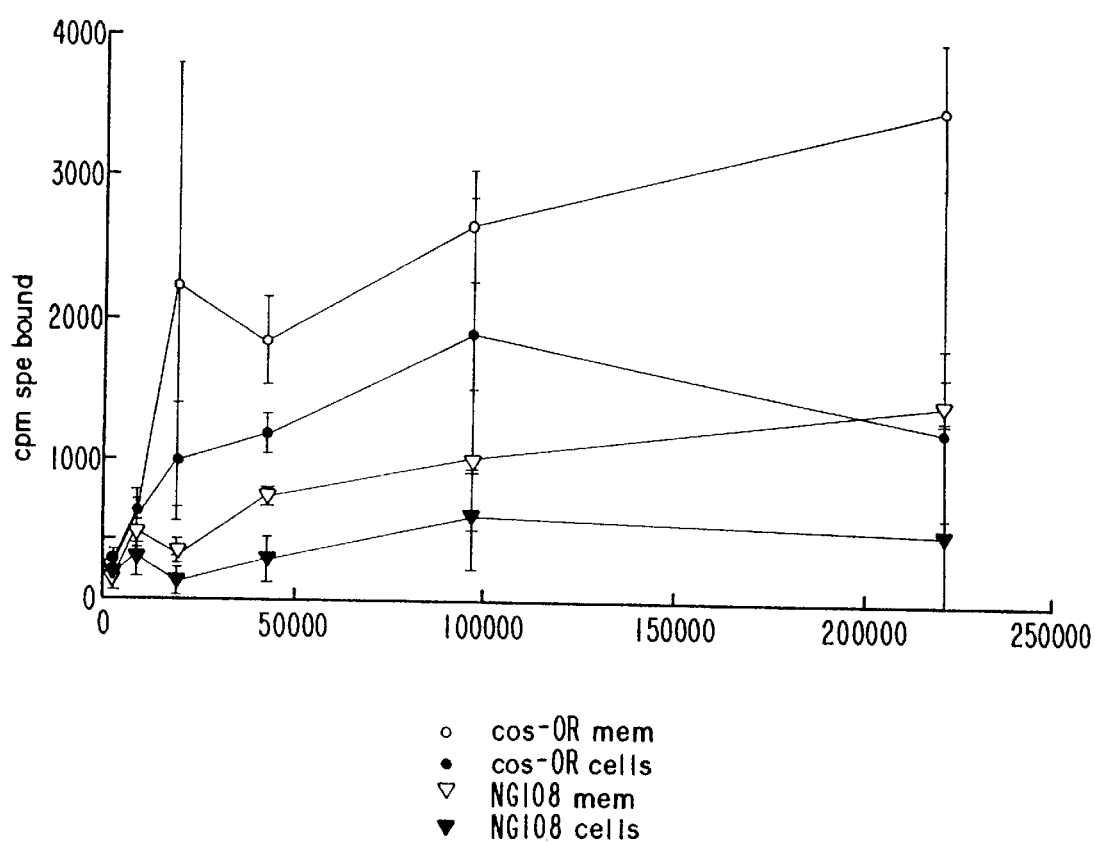
FIG. 1 depicts a comparison of binding of $^3$H-diprenorphine (saturation curves) between NG108-15 cells and COS cells three days following transfection (by electroporation) of each with DOR-1 in the CDM-8 vector. Specific opioid binding was undetectable in nontransfected COS cells or COS cells transfected with plasmid alone.

The invention provides DNA encoding mammalian opioid receptor protein and additional recombinant nucleic acids, expression vectors and methods useful for the production of these proteins. In addition, eucaryotic cells, such as COS cells, transformed with the recombinant molecules of the invention so as to express opioid receptor proteins at their surface are useful in screening assays to identify candidate opioid agonists and antagonists. In addition, antibodies may be raised to the recombinantly produced opioid receptor proteins. These antibodies are useful in immunoassays for said protein and in affinity purification thereof.

Recombinant Opioid Receptor

Illustrated hereinbelow is the obtention of a cDNA encoding a murine delta opioid receptor. The complete DNA sequence of the cDNA, and the amino acid sequence encoded thereby, are set forth herein in FIG. 5. The availability of this cDNA permits the retrieval of the corresponding opioid receptor-encoding DNA from other vertebrate species. Accordingly, the present invention places within the possession of the art, recombinant molecules and methods for the production of cells expressing opioid receptors of various types and of various vertebrate species. Thus, the cDNA of FIG. 5, or a portion thereof, may be used as a probe to identify that portion of vertebrate genomic DNA or cDNA which encodes an opioid receptor protein. Illustrative methods used to prepare a genomic library and identify the opioid receptor-encoding genes are described for convenience hereinbelow. Also exemplified as illustrating the method of the invention is the retrieval of human ORL-1 from a brain stem cDNA library.

The DOR-1 clone described in FIG. 5 is a cDNA clone corresponding to the murine delta opioid receptor. The present inventors found, and describe herein, that screening of a human genomic library under conditions of low stringency results in the recovery of DNA encoding all three types of human opioid receptors. Similarly, a murine genomic clone was obtained. In addition, a cDNA clone was obtained from a mouse brain library encoding the murine mu opioid receptor. Thus, either cDNA libraries from appropriate sources, such as brain, or genomic libraries, are fruitful sources or substrates for obtaining the DNA of the present invention and the corresponding recombinant materials. The invention is thus directed to DNA encoding an opioid receptor of a vertebrate, wherein the opioid receptor is encoded by a nucleotide sequence which hybridizes under conditions of low stringency to the nucleotide sequence shown in FIG. 5 or to its complement.

In the alternative, the DNA of FIG. 5 or a portion thereof may be used to identify specific tissues or cells which express opioid receptor protein by analyzing the MRNA, for example, using Northern blot techniques. Those tissues which are identified as containing mRNA encoding opioid receptor protein using the probes of the invention are then suitable sources for preparation of cDNA libraries which may further be probed using the cDNA described hereinbelow.

The DNA encoding the various vertebrate opioid receptor proteins, obtained in general as set forth above, according to the standard techniques described hereinbelow, can be used to produce cells which express the opioid receptor at their surface; such cells are typically eucaryotic cells, in particular, mammalian cells such as COS cells or CHO cells. Suitable expression systems in eucaryotic cells for such production are described hereinbelow. The opioid receptor proteins may also be produced in procaryotes or in alternative eucaryotic expression systems for production of the protein per se. The DNA encoding the protein may be ligated into expression vectors preceded by signal sequences to effect its secretion, or may be produced intracellularly, as well as at the cell surface, depending on the choice of expression system and host. If desired, the opioid receptor protein thus recombinantly produced may be purified using suitable means of protein purification, and, in particular, by affinity purification using antibodies or fragments thereof immunospecific for the opioid receptor protein.

The reader is reminded that the term "opioid receptor" as used herein includes not only the conventional delta, kappa and mu opioid receptors, but also opioid receptor-like proteins which interact with G proteins in a similar manner. These receptor-like proteins are useful in analogous ways, and offer additional screening tools for candidate compounds that affect the central nervous system. They are thus useful for the same purposes as the "conventional" receptors.

Screening for Opioid Agonists and Antagonists Using Recombinant Cells

The ability of a candidate compound to act as an opioid agonist or antagonist may be assessed using the recombinant cells of the invention in a variety of ways. To exhibit either agonist or antagonist activity, the candidate compound must bind to the opioid receptor. Thus, to assess the ability of the candidate to bind, either a direct or indirect binding assay may be used. For a direct binding assay, the candidate binding compound is itself detectably labeled, such as with a radioisotope or fluorescent label, and binding to the recombinant cells of the invention is assessed by comparing the acquisition of label by the recombinant cells to the acquisition of label by corresponding untransformed (control) cells.

More convenient, however, is the use of a competitive assay wherein the candidate compound competes for binding to the recombinant cells of the invention with a detectably labeled form of an opioid ligand known to bind to the receptor. Such ligands are themselves labeled using radioisotopes or fluorescent moieties, for example. A particularly suitable opioid known to bind to this receptor is diprenorphine. A typical protocol for such an assay is as follows:

In general, about $10^6$ recombinant cells are incubated in suspension in 1.0 ml of Kreb's Ringer Hepes Buffer (KRHB) at pH 7.4, 37° C. for 20 min with $^3$H-diprenorphine. Nonspecific binding is determined by the addition of 400 nM diprenorphine in the binding mixtures. Various concentrations of candidate compounds are added to the reaction mixtures. The incubations are terminated by collecting the cells on Whatman GF-B filters, with removal of excess radioactivity by washing the filters three times with 5 ml of KRHB at 0° C. After incubating at 20° C. overnight in 5 ml of scintillation fluid, such as Liquiscint (National Diagnostics, Somerville, N.J.), the radioactivity on the filters is determined by liquid scintillation counting.

The $K_d$ (dissociation constant) values for the candidate opiate ligands can be determined from the $IC_{50}$ value ("inhibitory concentration$_{50}$" means the concentration of candidate ligand that results in a 50% decrease in binding of labeled diprenorphine).

The effects of sodium and GTP on the binding of ligands to the recombinantly expressed receptors can be used to distinguish agonist from antagonist activities. If the binding of a candidate compound is sensitive to Na$^+$ and GTP, it is more likely to be an agonist than an antagonist, since the functional coupling of opioid receptors to second messenger molecules such as adenylate cyclase requires the presence of both sodium and GTP (Blume et al., *Proc Natl Acad Sci USA* (1979) 73:26–35). Furthermore, sodium, GTP, and GTP analogues have been shown to effect the binding of opioids and opioid agonists to opioid receptors (Blume, *Life Sci* (1978) 22:1843–52). Since opioid antagonists do not exhibit binding that is sensitive to guanine nucleotides and sodium, this effect is used as a method for distinguishing agonists from antagonists using binding assays.

In addition, agonist activity can directly be assessed by the functional result within the cell. For example, it is known that the binding of opioid agonists inhibits cAMP formation, inhibits potassium channel activation, inhibits calcium channel activation, and stimulates GTPase. Assessment of these activities in response to a candidate compound is diagnostic of agonist activity. In addition, the ability of a compound to interfere with the activating activity of a known agonist such as etorphine effectively classifies it as an antagonist.

In one typical assay, the measurement of cAMP levels in cells expressing opioid receptors is carried out by determining the amount of $^3$H-cAMP formed from intracellular ATP pools prelabeled with $^3$H-adenine (Law et al., supra). Thus, cAMP formation assays are carried out with $0.5 \times 10^6$ cells/ 0.5 ml of KRHB at pH 7.4, incubated at 37° C. for 20 minutes. After addition of the internal standard $^{32}$P-cAMP, the radioactive cAMP is separated from other $^3$H-labeled nucleotides by known double-column chromatographic methods. The opiate agonists' ability to inhibit cAMP accumulation is then determined as described by Law et al. (supra).

The potency of a candidate opiate antagonist can be determined by measuring the ability of etorphine to inhibit cyclic AMP accumulation in the presence and in the absence of known amounts of the candidate antagonist. The inhibition constant ($K_i$) of an antagonist can then be calculated from the equation for competitive inhibitors.

An interesting feature of screening assays using the prior art NG108-15 cells is that the agonist adenylate cyclase inhibition function apparently does not require binding of all receptors on these cells. Thus, the $K_d$ and $K_i$ values for the opioid ligands differed when using these cells.

The foregoing assays, as described above, performed on the recombinantly transformed cells of the present invention, provide a more direct and more convenient screen for candidate compounds having agonist and antagonist opioid receptor activity than that previously available in the art. Furthermore, such assays are more sensitive since cells can, in accordance with the present invention, be engineered to express high levels of the opioid receptor. Additionally, cells engineered in accordance with the present invention will circumvent the concern that NG108-15 cells, due to their tumor cell background, have a cellular environment that artifactually affects opioid receptor expression.

The mu opioid encoding DNA described herein also offer a means to follow inheritance patterns. DNA sequence polymorphisms frequently occur in the noncoding regions that surround genes. Polymorphisms are especially frequent in repeat sequences such as CACACA which often show distinct polymorphisms in the number of repeats that are present in different individuals. These polymorphisms offer a marker by which to follow the inheritance of the gene among family members. The inheritance of a gene (such as MORa) or its human counterpart can be followed by polymerase chain reaction (PCR) amplification of the region surrounding the CACACA polymorphism and analyzing the resulting products. This would be a useful diagnostic marker for the mu opioid receptor gene.

Methods to Prepare Opioid Receptor Protein or Portions Thereof

The present invention provides the amino acid sequence of a murine opioid receptor; similarly, the availability of the cDNA of the invention places within possession of the art corresponding vertebrate opioid receptors whose amino acid sequence may also be determined by standard methods. As the amino acid sequences of such opioid receptors are known, or determinable, in addition to purification of such receptor protein from native sources, recombinant production or synthetic peptide methodology may also be employed for producing the receptor protein or peptide.

The opioid receptor or portions thereof can thus also be prepared using standard solid phase (or solution phase) peptide synthesis methods, as is known in the art. In addition, the DNA encoding these peptides may be synthesized using commercially available oligonucleotide synthesis instrumentation for production of the protein in the manner set forth above. Production using solid phase peptide synthesis is, of course, required if amino acids not encoded by the gene are to be included.

The nomenclature used to describe the peptides and proteins of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $NH_3^+$ and C-terminal $COO^-$ at physiological pH are understood to be present though not necessarily specified and shown, either in specific examples or in generic formulas. Free functional groups on the side chains of the amino acid residues may also be modified by glycosylation, phosphorylation, cysteine binding, amidation, acylation or other substitution, which can, for example, alter the physiological, biochemical, or biological properties of the compounds without affecting their activity within the meaning of the appended claims.

In the peptides shown, each gene-encoded residue, where appropriate, is represented by a single letter designation, corresponding to the trivial name of the amino acid, in accordance with the following conventional list:

| Amino Acid | One-Letter Symbol | Three-letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Nomenclature of Enkephalins

Enkephalins are either of two peptides having five residues with the N-terminal residue numbered 1:

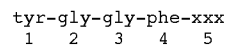

```
tyr-gly-gly-phe-xxx
 1   2   3   4   5
```

In "met enkephalin" the fifth residue is methionine:
tyr-gly-gly-phe-met (SEQ ID NO:1)
In "leu enkephalin" the 5th residue is leucine:
tyr-gly-gly-phe-leu (SEQ ID NO:2)
Enkephalin analogs can be made with (1) amino acid substitutions, (2) D-amino acid substitutions, and/or (3) additional amino acids. The site at which the substitution is made is noted at the beginning of the compound name. For example, "(D-ala$^2$, D-leu$^5$) enkephalin" means that D-ala is present at the second position and D-leu is present at the fifth position:
tyr-[D-ala]-gly-phe-[D-leu] (SEQ ID NO:5)
One letter abbreviations can also be used. Thus, "(D-ser$^2$) leu enkephalin" could be abbreviated as "DSLE." Additional residues are noted as well. Thus, the addition of a threonine residue (to the sixth position) of (D-ser$^2$) leu enkephalin would be "(D-ser$^2$) leu enkephalin thr" which could be abbreviated as "DSLET":
tyr-[D-ser]-gly-phe-leu-thr (SEQ ID NO:3)

Antibodies

Antibodies immunoreactive with the opioid receptor protein or peptide of the present invention can be obtained by immunization of suitable mammalian subjects with peptides, containing as antigenic regions those portions of the receptor intended to be targeted by the antibodies. Certain protein sequences have been determined to have a high antigenic potential. Such sequences are listed in antigenic indices, for example, MacVector software (I.B.I.) Thus, by determining the sequence of the opioid receptor protein and evaluating the sequence with an antigenic index, probable antigenic sequences are located.

Antibodies are prepared by immunizing suitable mammalian hosts according to known immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the happen. The hapten peptides can be extended or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal antibody (mAb) preparations is preferred. Immortalized cell lines which secrete the desired mAbs may be prepared using the standard method of Kohler and Milstein or modifications which effect immortalization of lymphocytes or spleen cells, as is generally known. The immortalized cell lines secreting the desired mAbs are screened by immunoassay in which the antigen is the peptide hapten or is the opioid receptor itself displayed on a recombinant host cell. When the appropriate immortalized cell culture secreting the desired mAb is identified, the cells can be cultured either in vitro or by intraperitoneal injection into animals wherein the mAbs are produced in the ascites fluid.

The desired mAbs are then recovered from the culture supernatant or from the ascites fluid. In addition to intact antibodies, fragments of the mAbs or of polyclonal antibodies which contain the antigen-binding portion can be used as antagonists. Use of immunologically reactive antigen binding fragments, such as the Fab, Fab', of F(ab')$_2$ fragments, is often preferable, especially in a therapeutic context, as these fragments are generally less immunogenic than the whole immunoglobulin molecule.

Standard Methods

The techniques for sequencing, cloning and expressing DNA sequences encoding the amino acid sequences corresponding to a opioid receptor, e.g., polymerase chain reaction (PCR), synthesis of oligonucleotides, probing a cDNA library, transforming cells, constructing vectors, preparing antisense oligonucleotide sequences based on known sense nucleotide sequences, extracting messenger RNA, preparing cDNA libraries, and the like are well-established in the art. Ordinarily skilled artisans are familiar with the standard resource materials, specific conditions and procedures. The following paragraphs are provided for convenience, it being understood that the invention is limited only by the appended claims.

RNA Preparation and Northern Blot

RNA preparation is as follows: The samples used for preparation of RNA are immediately frozen in liquid nitrogen and then stored until use at −80° C. The RNA is prepared by CsCl centrifugation (Ausubel et al., supra) using a modified homogenization buffer (Chirgwin et al., *Biochemistry* (1979) 18:5294–5299). Poly(A$^+$) RNA is selected by oligo(dT) chromatography (Aviv and Leder, *Proc Natl Acad Sci USA* (1972) 69:1408–1412). RNA samples are stored at −80° C.

Analysis of gene expression and tissue distribution can be accomplished using Northern blots with, e.g., radiolabeled probes. The mRNA is size-separated using gel electrophoresis and then typically is transferred to a nylon membrane or to nitrocellulose and hybridized with radiolabeled probe. Presence of the hybridized probe is detected using autoradiography.

Cloning

The cDNA sequences encoding the opioid receptor protein are obtained from a random-primed, size-selected cDNA library.

Alternatively, the cDNA sequences encoding opioid receptor protein are obtained from a cDNA library prepared from MRNA isolated from cells expressing the receptor protein in various organs such as the brain, according to procedures described in Sambrook, J. et al., *MOLECULAR CLONING: A LABORATORY MANUAL*, 2nd Edition, Cold Spring Harbor Press, Cold Spring Harbor, N.Y., 1989.

The cDNA insert from the successful clone, excised with a restriction enzyme such as EcoRI, is then used as a probe of the original cDNA library or other libraries (low stringency) to obtain the additional clones containing inserts encoding other regions of the protein that together or alone span the entire sequence of nucleotides coding for the protein.

An additional procedure for obtaining cDNA sequences encoding the opioid receptor protein is PCR. PCR is used to amplify sequences from a pooled cDNA library of reversed-transcribed RNA, using oligonucleotide primers based on the transporter sequences already known.

Vector Construction

Construction of suitable vectors containing the desired coding and control sequences employs ligation and restriction techniques which are well understood in the art (Young et al., *Nature* (1988) 316:450–452). Double-stranded cDNA encoding opioid receptor protein is synthesized and prepared for insertion into a plasmid vector CDM8. Alternatively, vectors such as Bluescript$^2$ or Lambda ZAP$^2$ (Stratagene, San Diego, Calif.) or a vector from Clontech (Palo Alto, Calif.) can be used in accordance with standard procedures (Sambrook, J. et al., supra).

Site specific DNA cleavage is performed by treating with the suitable restriction enzyme, such as EcoRI, or more than one enzyme, under conditions which are generally understood in the art, and the particulars of which are specified by the manufacturer of these commercially available restriction enzymes. See, e.g., New England Biolabs, Product Catalog. In general, about 1 $\mu$g of DNA is cleaved by one unit of enzyme in about 20 $\mu$l of buffer solution; in the examples herein, typically, an excess of restriction enzyme is used to ensure complete digestion of the DNA substrate. Incubation times of about one to two hours at about 37° C. are workable, although variations can be tolerated. After each incubation, protein is removed by extraction with phenol/chloroform, and can be followed by other extraction and the nucleic acid recovered from aqueous fractions by precipitation with ethanol.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of Na$^+$ and Mg++ using about 1 unit of BAP or CIP per μg of vector at 60° C. or 37° C., respectively, for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Ligations are performed in 15–50 μl volumes under the following standard conditions and temperatures: 20 mM Tris-HCl, pH 7.5, 10 mM MgCl$_2$, 10 mM DTT, 33 μg/ml BSA, 10 mM to 50 mM NaCl, and either 40 AM ATP, 0.01–0.02 (Weiss) units T4 DNA ligase at 0° C. (for "sticky end"ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration. Correct ligations for vector construction are confirmed according to the procedures of Young et al., supra.

cDNA Library Screening cDNA libraries can be screened using reduced stringency conditions as described by Ausubel et al., *CURRENT PROTOCOLS IN MOLECULAR BIOLOGY*, Greene Publishing and Wiley-Interscience, New York (1990), or by using methods described in Sambrook et al. supra), or by using a colony or plaque hybridization procedure with a fragment of the DOR-1 cDNA coding for opioid receptor protein.

Plaque hybridization is typically carried out as follows: Host bacteria such as LE 392 (Stratagene) are grown overnight at 37° in LB Broth (Sambrook et al., supra), gently pelleted and resuspended in one half the original volume of 10 mM MgSO$_4$, 10 mM CaCl$_2$. After titration, an amount of the phage library containing approximately 50,000 plaque forming units (pfu) is added to 300 μl of the host bacteria, incubated at 37° for 15 minutes and plated onto NZYCM agar with 10 ml NZYCM top agarose. A total of a million plaques distributed on twenty 15 cm plates are screened. For colony screening, transfected bacteria are plated onto LB broth plates with the appropriate antibiotics. After the plaques or colonies have grown to 1 mm, the plates are chilled at 4° C. for at least two hours, and then overlaid with duplicate nitrocellulose filters, followed by denaturation of the filters in 0.5 M NaOH/1.5 M NaCl for five minutes and neutralization in 0.5 M Tris, pH 7.4/1.5 M NaCl for five minutes. The filters are then dried in air, baked at 80° C. for two hours, washed in 5×SSC/0.50 SDS at 68° C. for several hours, and prehybridized in 0.5 M NaPO$_4$, pH 7.2/1% BSA/1 mM EDTA/7% SDS/100 μg/ml denatured salmon sperm DNA for more than 4 hours. Using the DOR-1 cDNA (described herein) labeled by random priming as a probe, high stringency hybridization is carried out in the same solution at 68° C., and the temperature is reduced to 50–60° C. for lower stringency hybridization. After hybridization for 16–24 hours, the filters are washed first in 40 mM NaP$_4$, pH 7.2/0.5% BSA/5% SDS/1 mM EDTA twice for one hour each, then in 40 mM NaPO$_4$, pH 7.2/1% BSA/1 mM EDTA for one hour each, both at the same temperature as the hybridization (Boulton et al., *Cell*(1991) 65:663–675). The filters are then exposed to film with an enhancing screen at –70° C. for one day to one week.

Positive signals are then aligned to the plates, and the corresponding positive phage is purified in subsequent rounds of screening, using the same conditions as in the primary screen. Purified phage clones are then used to prepare phage DNA for subcloning into a plasmid vector for sequence analysis. Tissue distribution of DNA corresponding to the various independent clones is analyzed using Northern blots and in situ hybridization using standard methods. Function of the DNA is tested using expression in a heterologous eucaryotic expression system such as COS cells.

Expression of Opioid Receptor Protein

The nucleotide sequence encoding opioid receptor protein can be expressed in a variety of systems. The cDNA can be excised by suitable restriction enzymes and ligated into procaryotic or eucaryotic expression vectors for such expression.

For example, as set forth below, the cDNA encoding the protein is expressed in COS cells. To effect functional expression, the plasmid expression vector CDM8 (Aruffo and Seed, *Proc Natl Acad Sci USA* (1987) 84:8573–8577, provided by Drs. Aruffo and Seed (Harvard University, Boston, Mass.) was used. Alternatively, other suitable expression vectors such as retroviral vectors can be used.

Procaryotic and preferably eucaryotic systems can be used to express the opioid receptor. Eucaryotic microbes, such as yeast, can be used as hosts for mass production of the opioid receptor protein. Laboratory strains of Saccharomyces cerevisiae, Baker's yeast, are used most, although a number of other strains are commonly available. Vectors employing, for example, the 2μorigin of replication (Broach, *Meth Enz* (1983) 101:307), or other yeast compatible origins of replications (e.g., Stinchcomb et al., *Nature* (1979) 282:39); Tschempe et al., *Gene* (1980) 10:157; and Clarke et al., *Meth Enz* (1983) 101:300) can be used. Control sequences for yeast vectors include promoters for the synthesis of glycolytic enzymes (Hess et al., *J Adv Enzyme Req* (1968) 7:149; Holland et al., *Biochemistry* (1978) 17:4900). Additional promoters known in the art include the promoter for 3-phosphoglycerate kinase (Hitzeman et al., *J Biol Chem* (1980) 255:2073), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

Alternatively, genes encoding opioid receptor protein are expressed in eucaryotic host cell cultures derived from multicellular organisms. (See, e.g., *Tissue Cultures*, Academic Press, Cruz and Patterson, eds, (1973)). These systems have the additional advantage of the ability to splice out introns, and thus can be used directly to express genomic fragments. Useful host cell lines include amphibian oocytes such as *Xenopus oocytes*, COS cells, VERO and HeLa cells, Chinese hamster ovary (CHO) cells, and insect cells such as SF9 cells. Expression vectors for such cells ordinarily include promoters and control sequences compatible with mammalian cells such as, for example, the commonly used early and late promoters from baculovirus, vaccinia virus, Simian Virus 40 (SV40) (Fiers et al., *Nature* (1973) 273:113), or other viral promoters such as those derived from polyoma, Adenovirus 2, bovine papilloma virus, or avian sarcoma viruses. The controllable promoter, hMTII (Karin et al., *Nature* (1982) 299:797–802) may also be used. General aspects of mammalian cell host system transformations have been described by Axel, U.S. Pat. No. 4,399,216. It now appears, that "enhancer" regions are important in optimizing expression; these are, generally, sequences found upstream or downstream of the promoter region in noncoding DNA regions. Origins of replication can be obtained, if needed, from viral sources. However, integration into the chromosome is a common mechanism for DNA replication in eucaryotes.

If procaryotic systems are used, an intronless coding sequence should be used, along with suitable control sequences. The cDNA of opioid receptor protein can be excised using suitable restriction enzymes and ligated into procaryotic vectors along with suitable control sequences for such expression.

Procaryotes most frequently are represented by various strains of *E. coli*; however, other microbial species and strains may also be used. Commonly used procaryotic control sequences which are defined herein to include promoters for transcription initiation, optionally with an operator, along with ribosome binding site sequences, including such commonly used promoters as the β-lactamase (penicillinase) and lactose (lac) promoter systems (Chang et al., *Nature* (1977) 198:1056) and the tryptophan (trp) promoter system (Goeddel et al., *Nucl Acids Res* (1980) 8:4057) and the λ derived $P_L$ promoter and N-gene ribosome binding site (Shimatake et al., *Nature* (1981) 292:128).

Depending on the host cell used, transformation is carried out using standard techniques appropriate to such cells. The treatment employing calcium chloride, as described by Cohen, *Proc Natl Acad Sci USA* (1972) 69:2110 (1972) or by Sambrook et al. (supra), can be used for procaryotes or other cells which contain substantial cell wall barriers. For mammalian cells without such cell walls, the calcium phosphate precipitation method of Graham and van der Eb, *Virology* (1978) 54:546, optionally as modified by Wigler et al., *Cell* (1979) 16:777–785, or by Chen and Okayama, supra, can be used. Transformations into yeast can be carried out according to the method of Van Solingen et al., *J Bact* (1977) 130:946, or of Hsiao et al., *Proc Natl Acad Sci USA* (1979) 76:3829.

Other representative transfection methods include viral transfection, DEAE-dextran mediated transfection techniques, lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Modulation of Expression by Antisense Sequences

Alternatively, antisense sequences may be inserted into cells expressing opioid receptors as a means to modulate functional expression of the receptors encoded by sense oligonucleotides. The antisense sequences are prepared from known sense sequences (either DNA or RNA), by standard methods known in the art. Antisense sequences specific for the opioid receptor gene or RNA transcript can be used to bind to or inactivate the oligonucleotides encoding the opioid receptor.

Terminology

As used herein, the singular forms "a", "an" and "the" include plural reference unless the context clearly dictates otherwise. Thus, for example, reference to "a receptor" includes mixtures of such receptors, reference to "an opioid" includes a plurality of and/or mixtures of such opioids and reference to "the host cell" includes a plurality of such cells of the same or similar type and so forth.

Unless defined otherwise all technical and scientific terms used herein have the same meaning as commonly understood by one of ordinary skill in the art to which this invention belongs. The following examples are intended to illustrate but not to limit the invention. Temperatures are in ° C. and pressures at near atmospheric unless otherwise specified.

Preparation of Mono $^{125}$I-DADLE

DADLE (Peninsula Laboratories Inc.) was iodinated using the iodogen method (Maidment et al., in: *MICRODIALYSIS IN THE NEUROSCIENCES*, T. Robinson and J. Justice, eds., pp. 275–303 (Elsevier, 1991)). Both mono- and di-iodinated forms are produced. It has been reported that di-iodo-DADLE does not bind opiate receptors, due to the di-iodination of the tyrosine residue (Miller, R. J., et al., *Life Sci* (1978) 22:379–88). Accordingly, mono-iodinated DADLE is preferred. Mono-$^{125}$I-DADLE is also preferred because it has extremely high specific activity compared to DADLE labeled with other isotopes. Thus, exposure times on the order of days, rather than weeks or months can be used.

By employing a molar ratio of sodium iodide to peptide of approximately 1:100 when carrying out iodination, the yield of the preferred mono-iodinated DADLE was increased. Additionally, to further enhance the yield of the mono-iodinated form, iodinated DADLE (containing both mono- and di-iodinated forms) was purified by reverse-phase HPLC (Maidment et al., supra). Employing this procedure a single major radiolabeled peak of the mono-iodinated DADLE separated from di-iodinated and non-iodinated forms.

DADLE monolabeled with $^{125}$I is crucial to successful screening. Radiolabeled $^{125}$I-DADLE differs from DADLE in several important parameters: size, hydrophobicity, and binding affinity (slightly lower). The purification of mono-iodinated from di-iodinated and non-iodinated DADLE by the HPLC step yields a ligand with very high specific activity (approximately 2000 Ci/mmol). The specific activity of the mono-iodinated form is approximately 100 times greater than that obtained by using the unseparated mixture of mono-, di-, and non-iodinated DADLE. Monolabeled $^{125}$I-DADLE must be used within a few days of its preparation.

EXAMPLE 1

Preparation of DOR-1

The NG108-15 cell line (available from Dr. Christopher Evans, UCLA) comprises a homogeneous and enriched source of delta opioid receptors. Utilizing MRNA isolated from NG108-15, a random-primed, size-selected cDNA library was constructed in plasmid vector CDM8. The cDNA library was amplified in bacteria. The cDNA library was transfected into COS-7 cells by electroporation. Transiently transfected COS lawns were screened and selected with highly purified mono-$^{125}$I-2dAla, 5dLeu enkephalin ($^{125}$,-DADLE). Positive clones were identified by film autoradiography, and plasmids from these cells were recovered and amplified in bacteria. Thereafter, the plasmids were re-transfected into COS cells. Following three cycles of such plasmid enrichment, individual clones were transfected and a pure clone was identified that bound $^{125}$-DADLE.

A. Construction of the cDNA Library

RNA was prepared from NG108-15 cells by homogenization in 6 M guanidinium isothiocyanate, followed by centrifugation through cesium chloride (J. M. Chirgwin, et al., *Biochemistry* (1979) 18:5294). Poly-A$^+$ RNA was isolated by chromatography over oligo-dT-cellulose (H. Aviv and P. Leder, *Proc Natl Acad Sci USA* (1972) 69:1408). Using this RNA as a template, random hexamers were used to prime cDNA synthesis by avian myeloblastosis virus reverse transcriptase (Life Sciences Inc.). Second strand synthesis was accomplished with RNase-H and *E. coli* DNA polymerase (U. Gubler and B. J. Hoffman, *Gene* (1983) 24:263). The ends of the cDNAs were rendered blunt with T4 DNA polymerase and BstXI linkers were added. cDNA longer than 1.5 kb was selected by electrophoresis through 5% acrylamide followed by electro-elution. The 1.5 kb cDNA was ligated to the CDM8 vector (A. Aruffo and B. Seed, supra, and then transformed into MC-1061 bacteria by electroporation (W. J. Dower et al., *Nucl Acids Res* (1988) 16:6127). Accordingly, six pools of plasmid DNA were prepared from the original cDNA library of approximately $2 \times 10^6$ recombinants.

B. Plasmid Transfection by Electroporation and Expression in COS Cells

COS cells were grown at high density and were harvested in trypsin, then resuspended at $2 \times 10^7$/ml in 1.2×RPMI containing 20% fetal calf serum. These cells were then incubated for ten minutes at 4° C. with 20 μg recombinant plasmid DNA from the cDNA library described above, and then electroporated at 960 μF and 230 V in a 0.4 cm gap cuvette (BioRad). The cells were then incubated an additional ten minutes at 4° C., and then plated into Dulbecco's Modified Eagle's Medium (DMEM) plus 10% fetal calf serum (FCS).

C. Screening of Transfected COS Cells

The transfected COS cells as obtained above were grown for three days, then screened using radiolabeled mono $^{125}$I-DADLE. Transfected COS lawns were washed with PBS, then incubated at room temperature with 10–20 nM $^{125}$I-DADLE in KHRB containing 1% BSA. After 1 hour, the plates were washed rapidly several times with ice cold PBS then dried on ice with strong flow of forced cold air. Plates were exposed on Dupont Cronex film in cassettes at room temperature. Positive clones were identified by careful alignment of the film with the petri dish via low power microscopy.

DNA was removed from positive cells by solubilization in 0.1% SDS in TE containing 1 μg/μl tRNA delivered from a syringe attached to a capillary tube on a micromanipulator. Plasmids were purified from the extracted cells using the Hirt lysis procedure (Hirt, B., *J Mol Biol* (1967) 26:365–369), and electroporated into MC-1061 bacteria. The plasmids were purified then retransfected into COS cells. Following three such enriching cycles, individual plasmid clones were transfected into COS cells yielding a single clone, named the DOR-1 clone.

EXAMPLE 2

Characterization of DOR-1

The DOR-1 clone initially was characterized by screening cell membrane fractions, from cells expressing DOR-1, with the labelled DADLE it was found that binding of $^{125}$I DADLE was displaced by nanomolar concentrations of opiate alkaloids diprenorphine, morphine, etorphine, and by DADLE, DSLET and DPDPE. Dextrorphan (10 μM) did not displace the $^{125}$I DADLE, whereas its opioid-active enantiomer levorphanol did displace the radiolabeled DADLE. Additionally, the mu receptor-selective ligand DAGO (5 μM) did not displace the counts.

Figure 2:
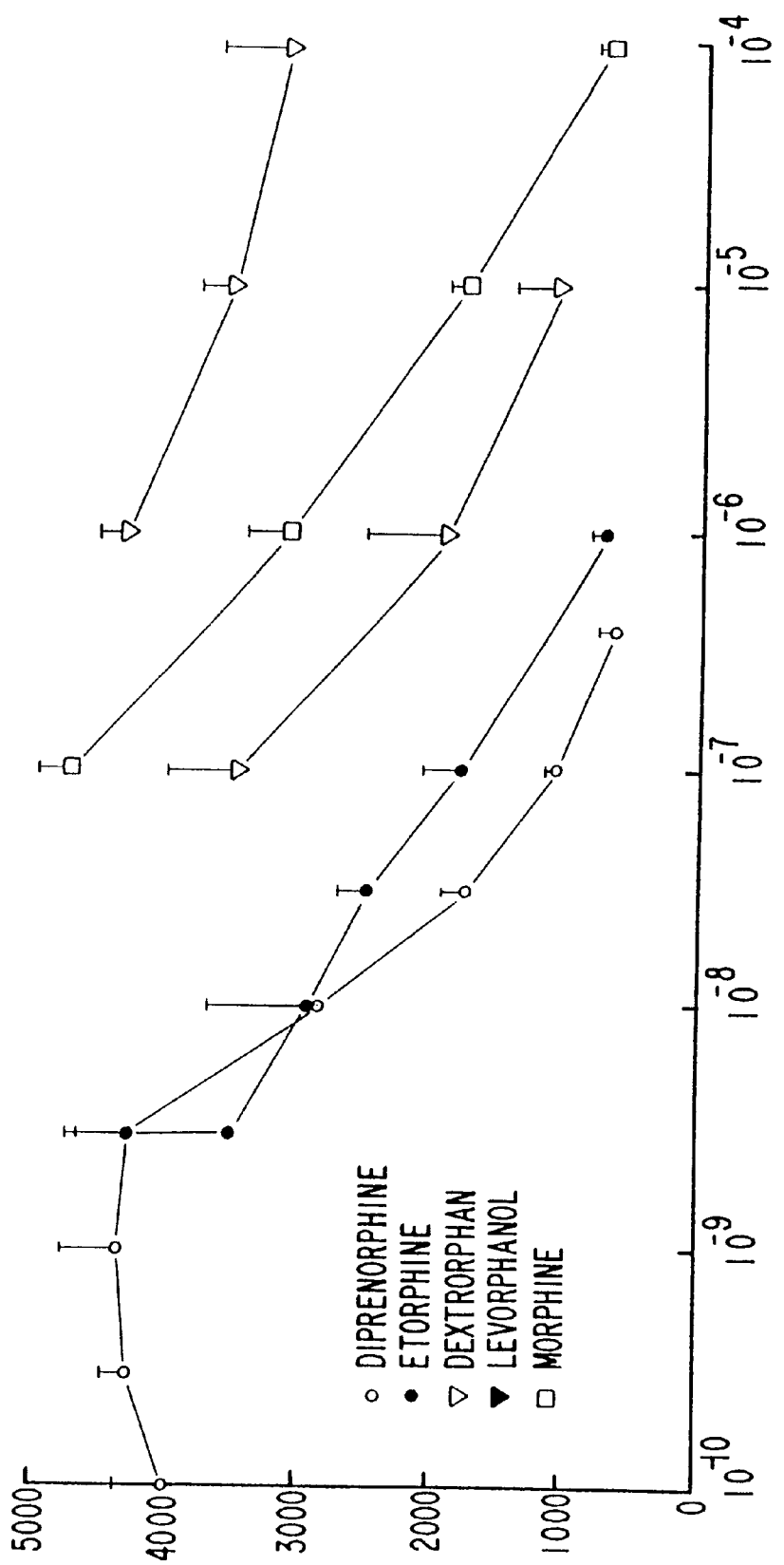
FIG. 2 depicts displacement curves of 5 nM $^3$H-diprenorphine from COS cell membranes of cells transfected with DOR-1.$^3$H-diprenorphine was displaced by diprenorphine, etorphine, morphine and levorphanol, but not by dextrorphan (the non-opiate active optical isomer of levorphanol).
Figure 3:
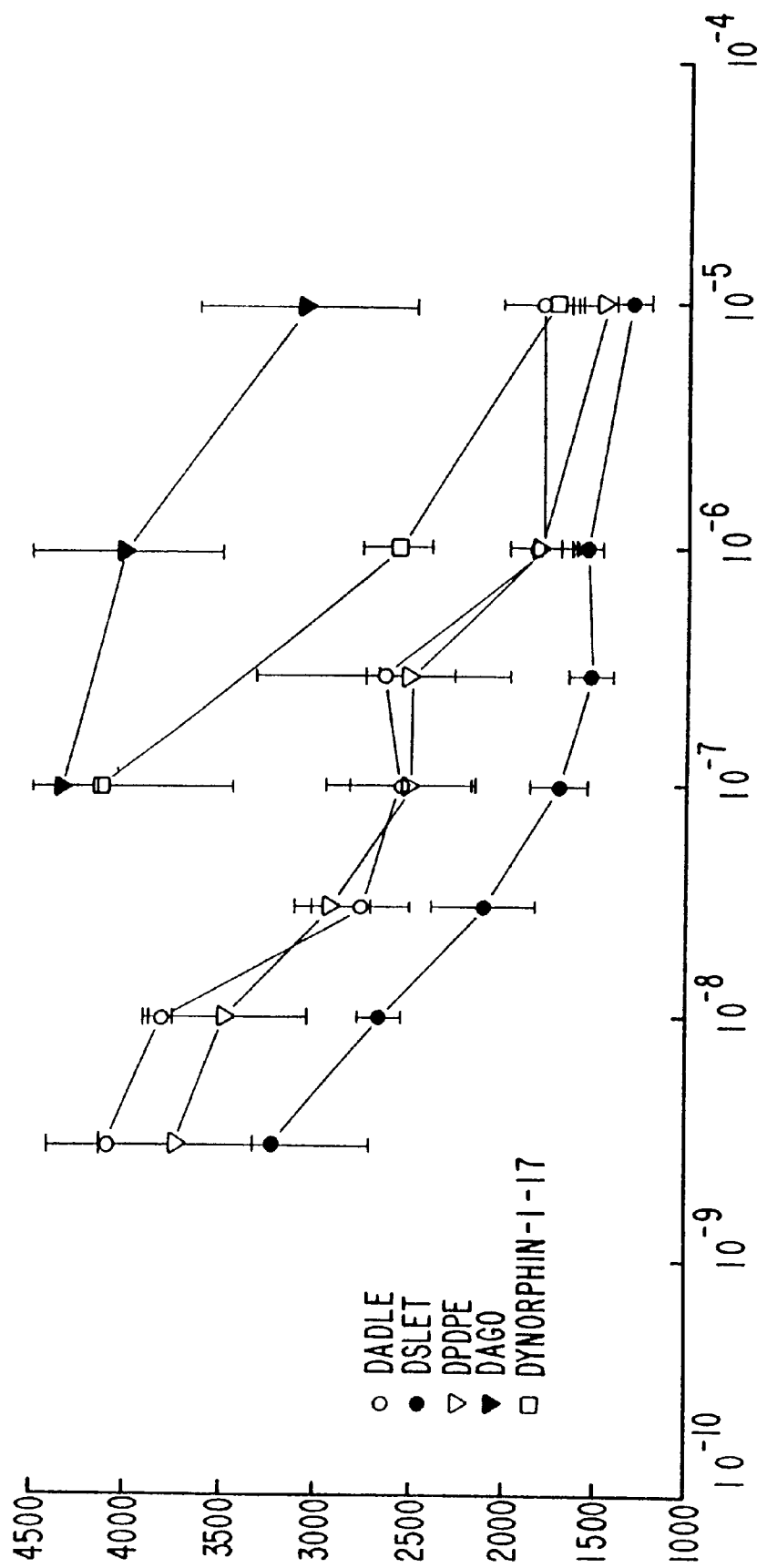
FIG. 3 depicts displacement curves of 5 nm $^3$H-diprenorphine from COS cell membranes of cells transfected with DOR-1. $^3$H-diprenorphine was displaced by DPDPE and DSLET, which are delta-selective agonists, by DADLE, a high affinity ligand for mu and delta receptors, and by dynorphin 1–17, a kappa-preferring ligand. $^3$H-diprenorphine was not displaced by DAGO, a mu-selective ligand.

The DOR-1 clone was further characterized pharmacologically by assessing binding of $^3$H-diprenorphine to intact cells expressing the DOR-1 clone (FIG. 1), and by assessing displacement of $^3$H-diprenorphine from membrane fractions of such cells (FIGS. 2 and 3).

Binding assays were conducted on intact cells in KRHB, 1% BSA; or on membranes in 25 mM HEPES, 5 mM MgCl$_2$ pH 7.7. Cells were harvested with PBS containing 1 mM EDTA, washed 2× with PBS then resuspended in KHRB. Membranes prepared from the cells (Law P. Y. E et al., *Mol Pharm* (1983) 23:26–35) were used directly in the binding assay. Binding assays were conducted in 96 well polypropylene cluster plates (Costar), at 4° C. in a total volume of 100 μl with an appropriate amount of radiolabeled ligand. Following 1 hour of incubation, plates were harvested on a Tomtec harvester and "B" type filtermats were counted in a Betaplate (Pharmacia) scintillation counter using Meltilex B/HS (Pharmacia) melt-on scintillator sheets.

Intact cells expressing DOR-1 were analyzed with the high affinity opiate antagonist $^3$H-diprenorphine. Specific binding was defined by the counts displaced by 400 nM diprenorphine. FIG. 1 shows a saturation curve for $^3$H-diprenorphine for NG108-15 cells, and COS-7 cells transfected with the delta opioid receptor clone. Untransfected COS cells, or COS cells transfected with plasmid having no insert showed no specific binding. Thus, the opioid binding of COS-DOR-1 cells was similar to that of NG108-15 cells.

Membranes prepared by standard methods from transfected COS-7 cells were employed for a more extensive pharmacological characterization of the receptor encoded by the DOR-1 clone. The affinities for the following alkaloid opiates in competition for 3H-diprenorphine are illustrated in FIG. 2: unlabeled diprenorphine, a high affinity antagonist for delta receptors; etorphine, a high affinity agonist for delta, mu and kappa receptors; levorphanol, a low affinity agonist for delta receptors; morphine, a low affinity agonist for delta receptors and a high affinity agonist for mu receptors; and dextrorphan, a non-opiate active enantiomer of levorphanol which should not bind delta receptors.

As shown in FIG. 2, the displacement of $^3$H-diprenorphine, in decreasing order of affinity, was observed with diprenorphine, etorphine, levorphanol and morphine. As expected, $^3$H-diprenorphine was not displaced by dextrorphan.

The affinities of the following opioid peptides in competition for $^3$H-diprenorphine are set forth in FIG. 3: DADLE, a high affinity agonist for mu and delta receptors; DSLET and DPDPE, both high affinity agonists of delta (but not mu) receptors; DAGO, a selective agonist for mu receptors; and Dynorphin 1–17, a high affinity agonist for kappa receptors and moderate to low affinity agonist for delta receptors. As shown in FIG. 3, the displacement of $^3$H-diprenorphine, in decreasing order of affinity, was observed for DSLET, DPDPE and DADLE, and Dynorphin 1–17. Only weak displacement by DAGO was observed.

EXAMPLE 3

Northern Blot Analysis of RNA

For Northern analysis, the MRNA from NG108-15 cells, and from cells dissected from regions of rat brain was separated by electrophoresis through 2.2 M formaldehyde/ 1.5' agarose, blotted to nylon and hybridized in aqueous solution at high stringency. The filters were prehybridized in 0.5 M $NaPO_4$, pH 7.2; 1% BSA; 1 mM EDTA; 7% SDS; and 100 µg/ml denatured salmon sperm DNA for at least four hours at 68° C. (Boulton et al., supra). The filters were then hybridized overnight under these same conditions with $\geq 5 \times 10^6$ cpm/ml purified cDNA insert labelled by random priming (A. P. Feinberg and B. Vogelstein, *Anal Biochem* (1983) 132:6). The filters were twice washed in 40 mM $NaPO_4$, pH 7.2; 0.5% BSA; 5% SDS; and 1 mM EDTA for one hour, and then washed twice in 40 mM $NaPO_4$, pH 7.2; 1% SDS; and 1 mM EDTA for one hour each, all at 68° C. Thereafter autoradiography was performed with DuPont Cromex Lightening Plus at −70° C.

Figure 4:
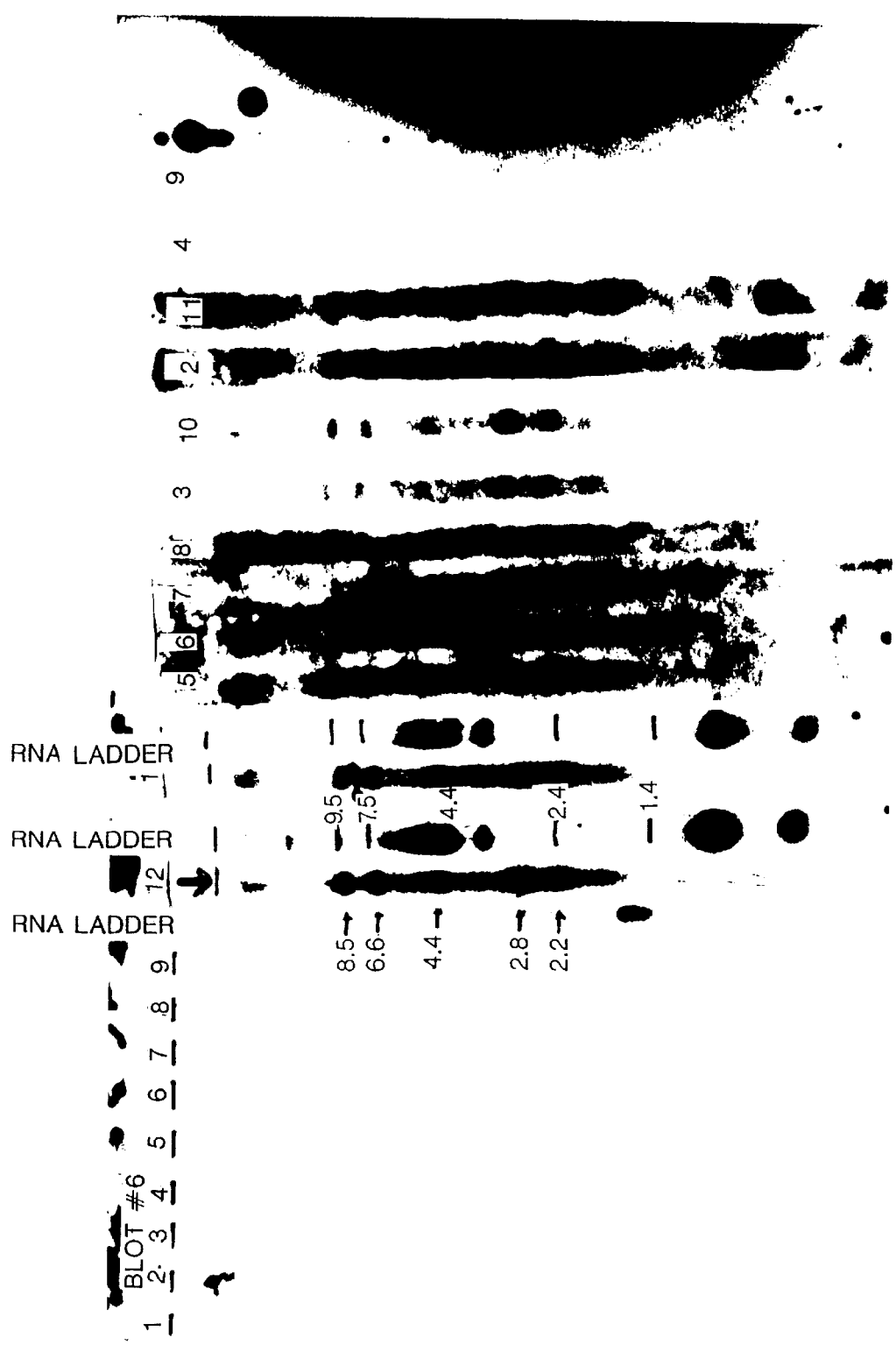
FIG. 4 depicts the results of a Northern analysis of MRNA from NG108-15 cells and cells from various rat brain regions.

The results of the Northern analysis of the mRNA showed the presence of multiple bands hybridizing to the probe at approximately 8.7, 6.8, 4.4, 2.75 and 2.2 kilobases (Kb) (FIG. 4). Also, the Northern analysis indicates that the pattern of mRNA may vary between brain regions. At present, it is unclear whether these mRNAs encode different protein sequences, and if so, whether these messages represent different types or sub-types of opioid receptors.

EXAMPLE 4

Southern Blot Analysis of DNA

Figure 7:
FIG. 7 depicts a Southern blot of radiolabeled DOR-1 cDNA probe hybridized at high stringency to NG108-15, mouse, rat and human DNA cut with BamHI.

The radiolabeled DOR-1 cDNA probe was hybridized to genomic Southern blots by standard methods (Sambrook et al., supra). Accordingly, the radiolabeled DOR-1 cDNA probe was hybridized under high stringency conditions to a blot of NG108-15, mouse, rat and human DNA cut with restriction endonuclease BamHI (FIG. 7). Single bands were observed in the clones containing the NG108-15, mouse, and rat DNA. The sizes of the bands hybridizing to the cDNA probe were estimated to be 5.2 kb (NG108-15), 5.2 kb (mouse), and 5.7 kb (rat). These results indicate the close homology of the mouse and rat genes, and also demonstrate that the DOR-1 clone is from the murine parent of the NG108-15 cell line.

In a blot containing EcoRI-cut genomic DNA from many different species, hybridization of the DOR-1 cDNA under conditions of moderate stringency showed two bands in each lane of mouse, rat, human, rabbit, and several other mammalian species. This demonstrates a close relationship between opioid receptor genes in all of these species. Further, these results show that the genes or cDNAs from each of these species may readily be cloned using hybridization under moderate stringency.

EXAMPLE 5

Determination of the cDNA Sequence

Isolated cDNA represented by the DOR clone was analyzed by subcloning the insert from the cDNA clone into a plasmid such as pBluescript™ (Stratagene, San Diego, Calif.) and using the dideoxy method (Sanger et al., *Proc Natl Acad Sci USA* (1977) 74:5463–5467). The sequence of the cDNA was determined from single-stranded DNA and specifically designed internal primers, using both Sequenase and ΔTaq cycle sequencing kits (USB). These kits, widely used in the art, utilize the dideoxy chain termination method. The DNA sequence and predicted protein sequence was then compared to sequences in established databanks such as GenBank.

Sequencing the cDNA insert in the DOR-1 clone, revealed an open reading frame of 370 amino acids (FIG. 5). Comparisons with known sequences in GenBank showed highest homology between DOR-1 and the G-protein-coupled somatostatin receptor (57% amino acid identity), and slightly lower homology with the receptors binding angiotensin, the two chemotactic factors IL-8 and N-formyl peptide. FIG. 6 shows the homology to the human somatostatin 1 receptor. The close homology of the present receptor clone with the somatostatin receptor is especially noteworthy since somatostatin ligands are reported to bind to opioid receptors, and to have molecular mechanisms similar to those in delta receptors.

Other features of the DOR-1 clone amino acid sequence deduced from the cDNA sequence include three consensus glycosylation sites at residues 18 and 33 (predicted to be in the extracellular N-terminal domain), and at residue 310 (close to the C-terminus and predicted to be intracellular). Phosphokinase C consensus sites are present within predicted intracellular domains, at residues 242, 255, 344, and 352. Seven putative membrane-spanning regions were identified based on hydrophobicity profiles, as well as homology with Rhodopsin and other G-protein coupled receptors which have been analyzed with respect to membrane-spanning regions using MacVector (I.B.I.) analysis. The DOR-1 clone isolated in accordance with the principles of the present invention produces a delta receptor with a predicted molecular weight of 40,558 daltons prior to post-translational modifications such as N-glycosylation.

EXAMPLE 6

Isolation of Opioid Receptor Genomic Clones

Isolation of genomic clones was carried out according to techniques known in the art. To isolate opiate receptor genomic clones, 300,000 human genomic clones in γgem 11 (Promega) and a similar number of mouse genomic clones in lambda Fix (Stratagene) were plated on host strain Le392 and probed with the 1.1 kb DOR-1 Pst/Xba I fragment, which contains primarily the coding region. The conditions for hybridization were of fairly low stringency: 50% formamide/6×SSC, overnight at 37° C. The washes were performed also at low stringency: 2×SSC, 0.1% SDS at room temperature.

One mouse clone and three human genomic clones were isolated and purified by sequential rounds of hybridization and plaque purification. DNA preparation and restriction analysis showed that the three human clones had very different EcoRI digestion patterns. The 1.1 kb opiate receptor probe hybridized to a different single EcoRI band in Southern blot analysis for each clone. These results indicated preliminarily that three different genes were represented by the human genomic clones which were designated H3, H14 and H20 (see FIGS. 8a, 8b, 8c and 8d). Each of these clones was deposited on Aug. 13, 1993 at the American Type Culture Collection, Rockville, Md., under conditions of the Budapest Treaty. All restrictions on access to these deposits will be irrevocably removed at the time a patent issues in the United States on the basis of this application. The ATCC deposit numbers are 75551 for H3 (δ), 75550 for H14 (κ), and 75549 for H20 (µ).

The H3, H14 and H20 clones were digested into smaller fragments by EcoRI and TaqI and then shotgun cloned into the appropriate site of Bluescript for sequencing. The partial nucleotide sequence for H3 is shown in FIG. 8a; the partial nucleotide sequence of H14 is shown in FIG. 8b; the partial nucleotide sequence of H20 is shown in FIG. 8c.

The three genomic clones were mapped by in situ hybridization on human metaphase chromosomes by Dr. Glenn Evans of the Salk Institute. H3 maps to chromosome 1P; H14 maps near the centromere of chromosome 8, and H20 maps to chromosome 6. Comparison of sequence data obtained as described above with the published sequences for the murine counterparts referenced hereinabove, and with the DOR-2 clone described hereinbelow, confirmed that: (a) H3 encodes the human delta opioid receptor; (b) H14 encodes the human kappa opioid receptor and (c) H20 encodes the human mu receptor. In addition, H20 appears to contain a CACACA marker (FIG. 8d) which provides a means to track the inheritance of this gene.

The genomic clones were digested into smaller fragments by EcoRI and TaqI, then shotgun cloned into the appropriate site of Bluescript for sequencing.

EXAMPLE 7

Isolation of Opioid Receptor Clones From Additional Organisms

In order to isolate the opioid receptor from mammalian brain cells, for example human brain cells, a random-primed human brainstem cDNA library in λ zap (Stratagene) was screened using the murine cDNA encoding the DOR-1 described herein. Positive plaques were purified and rescreened. Individual positive clones are sequenced and characterized as above.

EXAMPLE 8

Determination of Probable Antigenic Sequences

By evaluating the amino acid sequence of the opioid receptor encoded by DOR-1 with the MacVector (I.B.I.) antigenic index, and the antigenic index in accordance to Jameson, B. and H. Wolf, Comput Applic in Biosci (1988) 4:181–186, the following underlined sequences of the delta opioid receptor were determined to have a high antigenic potential:

NH$_2$MELVPSARAELOSSPLVNLSDAFPSAFPSAGAN
ASGSPGARSASSLALAIAITALYSAVCAVGLLGN
VLVMFGIVRYTKLKTATNIYIFNLALADALATST
LPFQSAKYLMETWPFGELLCKAVLSIDYYNMFT
SIFTLTMMSVDRYIAVCHPVKALDFRTPAKAKLI
NICIWVLASGVGVPIMVMAVTQPRDGAVVCML
QFPSPSWYWDTVTKICVFLFAFVVPILIITVCYG
LMLLRLRSVRLLSGSKEKDRSLRRITRMVLVVV
GAFVVCWAPIHIFVIVWTLVDINRRDPLVVAALH
LCIALGYANSSLNPVLYAFLDENFKRCFRQLCRT
PCGROEPGSLRRPROATTRERVTACTPSDGPGGG
AAA-COOH. (SEQ ID NO:2)

The N-terminal sequence is extracellular, the other four sequences are predicted to be intracellular.

EXAMPLE 9

Recovery of the Murine Clone DOR-2 (mMOR-1)

A cDNA library prepared from mouse brain in λt10 was probed using the low-stringency conditions of Example 6 using DOR-1 as a probe. One clone was recovered, inserted into Bluescript and sequenced. Northern and Southern blots indicated divergence from DOR-1. This clone, designated DOR-2, represented a new gene. DOR-2 hybridized to a different pattern of neurons than did DOR-1 and showed greater labeling of the striatum. Expression of DOR-1 by insertion into the vector PcDNA and transfection into mammalian cells produced cells which bind morphine, indicative of a mu-receptor. The cells also bind the nonselective opiate antagonist diprenorphine. The identity of DOR-2 (mMOR-1) as that of a mu receptor was confirmed by the displacement of $^3$H-DPN by nanomolar concentrations of the mu-selective ligands morphiceptin, DAMGO and morphine. The delta selective ligands DPDPE and deltorphan did not displace the binding and naloxone had the expected high affinity. The partial sequence designated H20, described in Example 6, was substantially similar to DOR-2. The partial sequence of DOR-2 is shown in FIG. 9.

FIG. 10 shows a comparison of the amino acid sequences of murine delta receptin with the rat mu and kappa receptors. There are extensive regions of homology.

EXAMPLE 10

Isolation of ORL-1

A human brain stem cDNA library was obtained from Stratagene and probed using low-stringency hybridization with the murine DOR-1 sequence shown in FIG. 5 under stringency conditions of 50% formamide/6×SSC at 37° C. with washes of 1 ×SSC/0.1% SDS at 37° C. A partial cDNA clone encoding ORL-1 was obtained and completed at the 5' end by RACE using cDNA obtained from human brain. The DNA sequence obtained for ORL-1 is shown in FIG. 11 and is identical to that reported by Mollereau et al. (supra). ORL-1 has approximately 44% amino acid identity to the mu receptor.

In addition to ORL-1, three clones for ORL-2 were obtained and a full-length clone was assembled from two overlapping clones. The sequence of one of the ORL-2 clones was identical to that reported by O'Dowd et al. (supra) while the other had a base change at Leu$^{129}$ which did not result in an alteration of amino acid sequence.

FIG. 12 compares the protein sequences of three cloned opioid receptors and ORL-1 and ORL-2.

Multiple PKC and PKA cites in the third intracellular loop of ORL-1 are similar to those in the delta opioid receptor. However, a His residue present in the sixth transmembrane domain of all the opioid receptors is absent in ORL-1; this His residue may play a role in aromatic interaction with ligands and may be critical for opioid receptor binding.

Mollereau et al. (supra) have shown that a stable cell line transfected with ORL-1 shows etorphine-induced cyclase inhibition. This inhibition is reversible with diprenorphine, although labeled diprenorphine binding to ORL-1 has not been shown. In addition, ORL-1 has two Asn-linked glycosylation sites in the N-terminal extracellular domain as shown in FIG. 12.

What is claimed is:

1. A method to screen a candidate substance for opioid agonist activity, which method comprises:
   (a) incubating cells displaying opioid receptor in the presence and absence of the candidate substance under conditions suitable for detection of activation of said opioid receptor, and
   (b) detecting the amount of activation of said opioid receptor in the presence as compared to the absence of said candidate substance;
   whereby an increase in the amount of activity in the presence, as compared to the absence of said candidate substance indicates that the substance is an agonist for said opioid receptor
   wherein said opioid receptor is produced and displayed on said cells by a method which comprises culturing said host cells which have been modified to contain an expression cassette which produces said opioid receptor in the host cells, said expression cassette comprising a nucleotide sequence encoding said opioid receptor operably linked to control sequences operable to provide expression in said host cells, and
   wherein said opioid receptor is a mammalian opioid receptor which is able to transduce a signal when contacted with an opioid agonist and is encoded by a nucleotide sequence which hybridizes under conditions of high stringency to the nucleotide sequence of SEQ. ID. NO: 7 or the complement thereof, wherein said conditions of high stringency comprise final wash steps of washing twice in 40 mM NaPO$_4$, pH 7.2; 0.5% BSA; 5% SDS; and 1 mM EDTA for one hour at 68° C. followed by final wash steps of washing twice in 40 mM NaPO$_4$, pH 7.2; 1% SDS; and 1 mM EDTA for one hour at 68° C.

2. A mammalian opioid receptor displayed at the surface of recombinant host cells and produced by a method which comprises culturing said host cells which have been modified to contain an expression cassette which produces said opioid receptor in the host, said expression cassette comprising a nucleotide sequence encoding said opioid receptor operably linked to heterologous control sequences operable in said host, wherein said opioid receptor is defined as able to transduce a signal when contacted with an opioid agonist and is encoded by a nucleotide sequence which hybridizes under conditions of high stringency to the nucleotide sequence of SEQ. ID. NO: 7 or the complement thereof, wherein said conditions of high stringency comprise final wash steps of washing twice in 40 mM NaPO$_4$, pH 7.2; 0.5% BSA; 5% SDS; and 1 mM EDTA for one hour at 68° C. followed by final wash steps of washing twice in 40 mM NaPO$_4$, pH 7.2; 1% SDS; and 1 mM EDTA for one hour at 68° C.

3. A method to screen a candidate substance for opioid antagonist activity, which method comprises:
(a) incubating cells displaying opioid receptor in the presence of an opioid agonist and in the presence and absence of the candidate substance under conditions suitable for detection of activation of said receptor and
(b) detecting the amount of activation of said receptor in the presence as compared to the absence of the candidate substance;
whereby a decrease in the amount of activation in the presence as compared to the absence of said candidate substance indicates that said candidate substance is an antagonist for said opioid receptor
wherein said opioid receptor is produced and displayed on said cells by a method which comprises culturing said host cells which have been modified to contain an expression cassette which produces said opioid receptor in the host cells, said expression cassette comprising a nucleotide sequence encoding said opioid receptor operably linked to control sequences operable to provide expression in said host cells, and wherein said opioid receptor is a mammalian opioid receptor which is able to transduce a signal when contacted with an opioid agonist and is encoded by a nucleotide sequence which hybridizes under conditions of high stringency to the nucleotide sequence of SEQ. ID. NO: 7 or the complement thereof, wherein said conditions of high stringency comprise washing twice in 40 mM $NaPO_4$, pH 7.2; 0.5% BSA; 5% SDS; and 1 mM EDTA for one hour at 68° C. followed by final wash steps of washing twice in 40 mM $NaPO_4$, pH 7.2; 1% SDS; and 1 mM EDTA for one hour at 68° C.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
       (A) LENGTH: 5 amino acids
       (B) TYPE: amino acid
       (C) STRANDEDNESS: single
       (D) TOPOLOGY: linear (xi) SEQUENCE DESCRIPTION: SEQ ID NO:1:

Tyr Gly Gly Phe Met
1               5

(2) INFORMATION FOR SEQ ID NO:2:

(i) SEQUENCE CHARACTERISTICS:
       (A) LENGTH: 5 amino acids
       (B) TYPE: amino acid
       (C) STRANDEDNESS: single
       (D) TOPOLOGY: linear (xi) SEQUENCE DESCRIPTION: SEQ ID NO:2:

Tyr Gly Gly Phe Leu
1               5

(2) INFORMATION FOR SEQ ID NO:3:

(i) SEQUENCE CHARACTERISTICS:
       (A) LENGTH: 6 amino acids
       (B) TYPE: amino acid
       (C) STRANDEDNESS: single
       (D) TOPOLOGY: linear (ix) FEATURE:
       (A) NAME/KEY: Modified-site
       (B) LOCATION: 2
       (D) OTHER INFORMATION: /product= "OTHER"
           /note= "D-Ser"

(xi) SEQUENCE DESCRIPTION: SEQ ID NO:3:

Tyr Xaa Gly Phe Leu Thr
1               5

(2) INFORMATION FOR SEQ ID NO:4:

(i) SEQUENCE CHARACTERISTICS:
       (A) LENGTH: 5 amino acids
       (B) TYPE: amino acid
       (C) STRANDEDNESS: single
       (D) TOPOLOGY: linear (ix) FEATURE:
       (A) NAME/KEY: Modified-site
       (B) LOCATION: group(2, 5)
       (D) OTHER INFORMATION: /product= "OTHER"
           /note= "D-penicillamine"

(xi) SEQUENCE DESCRIPTION: SEQ ID NO:4:

Tyr Xaa Gly Phe Xaa
1               5

(2) INFORMATION FOR SEQ ID NO:5:

(i) SEQUENCE CHARACTERISTICS:

(A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /product= "OTHER"
            /note= "D-Ala"

(ix) FEATURE:
        (A) NAME/KEY: Modified-site
        (B) LOCATION: 5
        (D) OTHER INFORMATION: /product= "OTHER"
            /note= "D-Leu"

(xi) SEQUENCE DESCRIPTION: SEQ ID NO:5:

Tyr Xaa Gly Phe Xaa
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /product= "OTHER"
            /note= "D-Ala"

(ix) FEATURE:
        (A) NAME/KEY: Modified-site
        (B) LOCATION: 4
        (D) OTHER INFORMATION: /product= "MePhe"
            /note= "N-Methylphenylalanine"

(ix) FEATURE:
        (A) NAME/KEY: Modified-site
        (B) LOCATION: 5
        (D) OTHER INFORMATION: /product= "Gly-ol"
            /note= "Carboxy end of glycine has been replaced with an
            alcohol substituent"

(xi) SEQUENCE DESCRIPTION: SEQ ID NO:6:

Tyr Xaa Gly Xaa Xaa
1               5

(2) INFORMATION FOR SEQ ID NO:7:

(i) SEQUENCE CHARACTERISTICS:
        (A) LENGTH: 1829 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 29..1144

(xi) SEQUENCE DESCRIPTION: SEQ ID NO:7:

```
GCACGGTGGA GACGGACACG GCGGCGCC ATG GAG CTG GTG CCC TCT GCC CGT         52
                              Met Glu Leu Val Pro Ser Ala Arg
                                1               5

GCG GAG CTG CAG TCC TCG CCC CTC GTC AAC CTC TCG GAC GCC TTT CCC       100
Ala Glu Leu Gln Ser Ser Pro Leu Val Asn Leu Ser Asp Ala Phe Pro
     10              15                  20

AGC GCC TTC CCC AGC GCG GGC GCC AAT GCG TCG GGG TCG CCG GGA GCC       148
```

```
Ser Ala Phe Pro Ser Ala Gly Ala Asn Ala Ser Gly Ser Pro Gly Ala
 25                  30                  35                  40

CGT AGT GCC TCG TCC CTC GCC CTA GCC ATC GCC ATC ACC GCG CTC TAC       196
Arg Ser Ala Ser Ser Leu Ala Leu Ala Ile Ala Ile Thr Ala Leu Tyr
                 45                  50                  55

TCG GCT GTG TGC GCA GTG GGG CTT CTG GGC AAC TGT CTC GTC ATG TTT       244
Ser Ala Val Cys Ala Val Gly Leu Leu Gly Asn Cys Leu Val Met Phe
             60                  65                  70

GGC ATC GTC CGG TAC ACC AAA TTG AAG ACC GCC ACC AAC ATC TAC ATC       292
Gly Ile Val Arg Tyr Thr Lys Leu Lys Thr Ala Thr Asn Ile Tyr Ile
         75                  80                  85

TTC AAT CTG GCT TTG GCT GAT GCG CTG GCC ACC AGC ACG CTG CCC TTC       340
Phe Asn Leu Ala Leu Ala Asp Ala Leu Ala Thr Ser Thr Leu Pro Phe
     90                  95                 100

CAG AGC GCC AAG TAC TTG ATG GAA ACG TGG CCG TTT GGC GAG CTG CTG       388
Gln Ser Ala Lys Tyr Leu Met Glu Thr Trp Pro Phe Gly Glu Leu Leu
105                 110                 115                 120

TGC AAG GCT GTG CTC TCC ATT GAC TAC TAC AAC ATG TTC ACT AGC ATC       436
Cys Lys Ala Val Leu Ser Ile Asp Tyr Tyr Asn Met Phe Thr Ser Ile
                125                 130                 135

TTC ACC CTC ACC ATG ATG AGC GTG GAC CGC TAC ATT GCT GTC TGC CAT       484
Phe Thr Leu Thr Met Met Ser Val Asp Arg Tyr Ile Ala Val Cys His
            140                 145                 150

CCT GTC AAA GCC CTG GAC TTC CGG ACA CCA GCC AAG GCC AAG CTG ATC       532
Pro Val Lys Ala Leu Asp Phe Arg Thr Pro Ala Lys Ala Lys Leu Ile
        155                 160                 165

AAT ATA TGC ATC TGG GTC TTG GCT TCA GGT GTC GGG GTC CCC ATC ATG       580
Asn Ile Cys Ile Trp Val Leu Ala Ser Gly Val Gly Val Pro Ile Met
    170                 175                 180

GTC ATG GCA GTG ACC CAA CCC CGG GAT GGT GCA GTG GTA TGC ATG CTC       628
Val Met Ala Val Thr Gln Pro Arg Asp Gly Ala Val Val Cys Met Leu
185                 190                 195                 200

CAG TTC CCC AGT CCC AGC TGG TAC TGG GAC ACT GTG ACC AAG ATC TGC       676
Gln Phe Pro Ser Pro Ser Trp Tyr Trp Asp Thr Val Thr Lys Ile Cys
                205                 210                 215

GTG TTC CTC TTT GCC TTC GTG GTG CCG ATC CTC ATC ATC ACG GTG TGC       724
Val Phe Leu Phe Ala Phe Val Val Pro Ile Leu Ile Ile Thr Val Cys
            220                 225                 230

TAT GGC CTC ATG CTA CTG CGC CTG CGC AGC GTG CGT CTG CTG TCC GGT       772
Tyr Gly Leu Met Leu Leu Arg Leu Arg Ser Val Arg Leu Leu Ser Gly
        235                 240                 245

TCC AAG GAG AAG GAC CGC AGC CTG CGG CGC ATC ACG CGC ATG GTG CTG       820
Ser Lys Glu Lys Asp Arg Ser Leu Arg Arg Ile Thr Arg Met Val Leu
    250                 255                 260

GTG GTG GTG GGC GCC TTC GTG GTG TGC TGG GCG CCC ATC CAC ATC TTC       868
Val Val Val Gly Ala Phe Val Val Cys Trp Ala Pro Ile His Ile Phe
265                 270                 275                 280

GTC ATC GTC TGG ACG CTG GTG GAC ATC AAT CGG CGC GAC CCA CTT GTG       916
Val Ile Val Trp Thr Leu Val Asp Ile Asn Arg Arg Asp Pro Leu Val
                285                 290                 295

GTG GCC GCA CTG CAC CTG TGC ATT GCG CTG GGC TAC GCC AAC AGC AGC       964
Val Ala Ala Leu His Leu Cys Ile Ala Leu Gly Tyr Ala Asn Ser Ser
            300                 305                 310

CTC AAC CCG GTT CTC TAC GCC TTC CTG GAC GAG AAC TTC AAG CGC TGC      1012
Leu Asn Pro Val Leu Tyr Ala Phe Leu Asp Glu Asn Phe Lys Arg Cys
        315                 320                 325

TTC CGC CAG CTC TGT CGC ACG CCC TGC GGC CGC CAA GAA CCC GGC AGT      1060
Phe Arg Gln Leu Cys Arg Thr Pro Cys Gly Arg Gln Glu Pro Gly Ser
    330                 335                 340
```

```
CTC CGT CGT CCC CGC CAG GCC ACC ACG CGT GAG CGT GTC ACT GCC TGC    1108
Leu Arg Arg Pro Arg Gln Ala Thr Thr Arg Glu Arg Val Thr Ala Cys
345                 350                 355                 360

ACC CCC TCC GAC GGC CCG GGC GGT GGC GCT GCC GCC TGACCTACCC         1154
Thr Pro Ser Asp Gly Pro Gly Gly Gly Ala Ala Ala
                365                 370

GACCTTCCCC TTAAACGCCC CTCCCAAGTG AAGTGATCAG AGGCCACACC GAGCTCCCTG  1214

GGAGGCTGTG GCCACCACCA GGACAGCTAG AATTGGGCCT GCACAGAGGG GAGGCCTCCT  1274

GTGGGGACGG GCCTGAGGGA TCAAAGGCTC CAGGTTGGAA CGGTGGGGGT GAGGAAGCAG  1334

AGCTGGTGAT TCCTAAACTG TATCCATTAG TAAGGCCTCT CAATGGGACA GAGCCTCCGC  1394

CTTGAGATAA CATCGGGTTC TGGCCTTTTT GAACACCCAG CTCCAGTCCA AGACCCAAGG  1454

ATTCCAGCTC CAGAACCAGG AGGGGCAGTG ATGGGTCGA TGATTTGGTT TGGCTGAGAG   1514

TCCCAGCATT TGTGTTATGG GGAGGATCTC TCATCTTAGA GAAGAAAGGG GACAGGGCAT  1574

TCAGGCAAGG CAGCTTGGGG TTTGGTCAGG AGATAAGCGC CCCCCTTCCC TTGGGGGGAG  1634

GATAAGTGGG GGATGGTCAC GTTGGAGAAG AGTCAAAGTT CTCACCACCT TTCTAACTAC  1694

TCAGCTAAAC TCGTTGAGGC TAGGGCCAAC GTGACTTCTC TGTAGAGAGG TACAAGCCGG  1754

GCCTGATGGG GCAGGCCTGT GTAATCCCAG TCATAGTGGA GGCTGAGGCT GGAAAATTAA  1814

GGACCAACAG CCCGG                                                  1829

(2) INFORMATION FOR SEQ ID NO:8:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:8:

Met Glu Leu Val Pro Ser Ala Arg Ala Glu Leu Gln Ser Ser Pro Leu
 1               5                  10                  15

Val Asn Leu Ser Asp Ala Phe Pro Ser Ala Phe Pro Ser Ala Gly Ala
                20                  25                  30

Asn Ala Ser Gly Ser Pro Gly Ala Arg Ser Ala Ser Ser Leu Ala Leu
        35                  40                  45

Ala Ile Ala Ile Thr Ala Leu Tyr Ser Ala Val Cys Ala Val Gly Leu
    50                  55                  60

Leu Gly Asn Cys Leu Val Met Phe Gly Ile Val Arg Tyr Thr Lys Leu
65                  70                  75                  80

Lys Thr Ala Thr Asn Ile Tyr Ile Phe Asn Leu Ala Leu Ala Asp Ala
                85                  90                  95

Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Leu Thr Met Met Ser Val
    130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Gln Pro Arg
            180                 185                 190
```

```
Asp Gly Ala Val Val Cys Met Leu Gln Phe Pro Ser Pro Ser Trp Tyr
        195                 200                 205

Trp Asp Thr Val Thr Lys Ile Cys Val Phe Leu Phe Ala Phe Val Val
        210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Gly Ala Phe Val Val
                260                 265                 270

Cys Trp Ala Pro Ile His Ile Phe Val Ile Val Trp Thr Leu Val Asp
        275                 280                 285

Ile Asn Arg Arg Asp Pro Leu Val Val Ala Ala Leu His Leu Cys Ile
290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Thr Pro
                325                 330                 335

Cys Gly Arg Gln Glu Pro Gly Ser Leu Arg Arg Pro Arg Gln Ala Thr
                340                 345                 350

Thr Arg Glu Arg Val Thr Ala Cys Thr Pro Ser Asp Gly Pro Gly Gly
                355                 360                 365

Gly Ala Ala Ala
        370

(2) INFORMATION FOR SEQ ID NO:9:

(i) SEQUENCE CHARACTERISTICS:
        (A) LENGTH: 369 amino acids
        (B) TYPE: amino acid
        (C) STRANDEDNESS: single
        (D) TOPOLOGY: linear (xi) SEQUENCE DESCRIPTION: SEQ ID NO:9:

Met Glu Leu Thr Ser Glu Gln Phe Asn Gly Ser Gln Val Trp Ile Pro
1               5                   10                  15

Ser Pro Phe Asp Leu Asn Gly Ser Leu Gly Pro Ser Asn Gly Ser Asn
                20                  25                  30

Gln Thr Glu Pro Tyr Tyr Asp Met Thr Ser Asn Ala Val Leu Thr Phe
                35                  40                  45

Ile Tyr Phe Val Val Cys Val Val Gly Leu Cys Gly Asn Thr Leu Val
        50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
                100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
        130                 135                 140

Val His Pro Ile Lys Ser Ala Lys Trp Arg Arg Pro Arg Thr Ala Lys
145                 150                 155                 160

Met Ile Asn Val Ala Val Trp Gly Val Ser Leu Leu Val Ile Leu Pro
```

```
                       165                 170                 175
Ile Met Ile Tyr Ala Gly Leu Arg Ser Asn Gln Trp Gly Arg Ser Ser
                180                 185                 190

Cys Thr Ile Asn Trp Pro Gly Glu Ser Gly Ala Trp Tyr Thr Gly Phe
            195                 200                 205

Ile Ile Tyr Ala Phe Ile Leu Gly Phe Leu Val Pro Leu Thr Ile Ile
        210                 215                 220

Cys Leu Cys Tyr Leu Phe Ile Ile Lys Val Lys Ser Ser Gly Ile
225                 230                 235                 240

Arg Val Gly Ser Ser Lys Arg Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Val Ala Ile Ser Pro Thr Pro
            275                 280                 285

Ala Leu Lys Gly Met Phe Asp Phe Val Val Ile Leu Thr Tyr Ala Asn
            290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Ala Glu
                325                 330                 335

Asp Gly Glu Arg Ser Asp Ser Lys Gln Asp Lys Ser Arg Leu Asn Glu
                340                 345                 350

Thr Thr Glu Thr Gln Arg Thr Leu Leu Asn Gly Asp Leu Gln Thr Ser
            355                 360                 365

Ile (2) INFORMATION FOR SEQ ID NO:10:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (xi) SEQUENCE DESCRIPTION: SEQ ID NO:10:

GGGCAGTGGT GTGCATGCTC CAGTTCCCCA GCCCCAGCTG GTACTGGGAC ACGGTGACCA      60

AGATCTGCGT GTTCCTCTTC GCCTTCGTGG TGCCCATCCT CATCATCACC GTGTGCTATG     120

GCCTCATGCT                                                            130

(2) INFORMATION FOR SEQ ID NO:11:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (xi) SEQUENCE DESCRIPTION: SEQ ID NO:11:

GGTGCAGTGG TATGCATGCT CCAGTTCCCC AGTCCCAGCT GGTACTGGGA CACTGTGACC      60

AAGATCTGCG TGTTCCTCTT TGCCTTCGTG GTGCCGATCC TCATCATCAC GGTGTGCTAT     120

GGCCTCATGC                                                            130

(2) INFORMATION FOR SEQ ID NO:12:

(i) SEQUENCE CHARACTERISTICS:
        (A) LENGTH: 2447 base pairs
```

(B) TYPE: nucleic acid
    (C) STRANDEDNESS: single
    (D) TOPOLOGY: linear (xi) SEQUENCE DESCRIPTION: SEQ ID NO:12:

```
CCTGGCCTTT TGGGGATGTG CTGTGCAAGA TAGTAATTTC CATTGATTAC TACAACATGT      60

TCACCAGCAT CTTCACCTTG ACCATGATGA GCGTGGACCG CTACATTGCC GTGTGCCACC     120

CCGTGAAGGC TTTGGACTTC CGCACACCCT TGAAGGCAAA GATCATCAAT ATCTGCATCT     180

GGCTGCTGTC GTCATCTGTT GGCATCTCTG CAATAGTCCT TGGAGGCACC AAAGTCAGGG     240

AAGGTAAGAG CAGTCATTTC ATTCTGTTCA TAAAAATGTA GCTTCAAATT ACATAGACTT     300

TTAATTTGAG CGTGAGTAGG CCACATATTT GTGGAAATCG ATGCCAAAAG ACGACGGAAA     360

TGTAGTGCCT AAATCCATGG AAGATGAGAA GTAGAACAAT TTTTTGTCCC TTTCCACCTC     420

TAAACACAGA ATGCAATAAT GACATTGCCA GAAGAGAGAT GCCCGACCTG TCTCCCATTC     480

TGGCAATGTT TAGTAGAAAG TGGAGGGGTG AGGATGAGGT AAGAACCACA GGCATGTAGA     540

TTTTAAAGTA CAACCTGGCA AGTCCAGACA CACCTTCTCA CTCCTTTTTT TCTCTTTAAC     600

AAGGGATATA AATTATTGGT GACATATGCT GGTTGTTTCC TCTTTTATTC CTAAAGGATA     660

ACCTCCAAAT CACTATTTTA ACAGCTTTGG CGTAGGATCT CAAAATCAAG TTAACGGATG     720

GTAGTTACAG ATGAGTCAGA ACCACTTGAT TTGGACATAT CAGGTTTTCC CTTGCAAACC     780

AGCCAACTGA TTTTTTTTTT TTTTTTTTTT GAGAGAGAGT CTTGCTCTGT TGCCAGGCTA     840

GAGTGCAGTG GCGCGATATC GGCTCACTGC AACCTCTGCC TCCCGGGTTC AACCTCAGCC     900

TCTCGAGTAG CTGGGACTAC TGGCACACAC CACCATGCCC AGCTAATTTT TGTATTTTTA     960

GTAGAGACAG GGTTTCACCG TGTTGGCCAG GGTGGTCTCA ATCTCTTGAC CTCGTGATCT    1020

GCCCGCCTCG NCTCCCCAAA GTGCTGGGAT TACAGGCGTG CNCTGCNCCC GNCCCCTGTT    1080

GATGTTTTTC CTGTATTTCT AGGACAGTAG TTCTCACTCT GGGCTGCACA TTGGAATCAC    1140

CTGGGTACTT TAGAAAACAC TGCTGCCTGC ATCCCACCCC TTAAGGGTCT GGTGTAATTG    1200

ACCTGGGGTA CAGCCTGGGT GTCAAGATTT TTGAGCTCTC TCCAGGTGAC TCTGACCTGC    1260

AGCCAAGGTG AGAGGTACTG TTCTAGGAGT TTTGCTTTAC TAGCAAAATA TAAAGCTATA    1320

GAAAGCATCT TTTGTTCCTC ATAGAAATTA ATGATGGGA GGTGAGCAGA ATAGTCACTC     1380

TGGGCCTACT CATGCTGTTT AATGCTCCAG CAGGTATATA GGTTCTCCAG TTACTAGGGG    1440

GTTCATAATA CCTGTGAGAG CAGATAACTG AGTGTATATA GTGAGGATTT CCAGGTCATA    1500

GTGAAAGGGC AAGGCACTAA AATCATAGCT TGTCTTGCAT ATACTGTTTG TTTGTTTTTA    1560

GACTTACATG TTAGGTTTCA GTTTACGTTT TAGGTTCACA GCAAAACTGA CCAGAAAGCA    1620

CAGAGAGGCA CTTCNATTTA CCTCCATTTA CCCCACACAG GCACATCCTC CCCTACAGAG    1680

TGGTCCATTT ATTACAGCTG CTGAACCCAC ACTGACACGC TGTTATCACT CAGAGCCTGG    1740

CAGTTTACAG AGGCTCACTC TCCGNTATGT GTCCTGTGNT TTGAACAAAT GTATAATGAC    1800

TTTATTCATT GTTTTTTAAT GAAGCTGATC TTTTCCCTCT GAAACTACAA AATGAATTTC    1860

TAGCATAGCC ATAGCAGGTG TCAAGCTATA CTACTAGGTA AATTTAAGA AATGCCCAAC     1920

TTTATCTATT TTGCATTTCA AAATATGATT AATCACACAT AGGATTTGT TCTTCATGC      1980

CTACAGCAAA TAGAAATAAA GTGCAAGAAA CTTTTCTGAG GCAAAGCTTT CACTTTGTGA    2040

ACGTAAAATG TTGACTCTAA TATTTTCCAT ACTGTAGTAT ATGTGTGTGT ATTATGTGAG    2100

GATTCATAGT CTGCTCTTAC TTTTTTATAG TAGCTAAGAA TTATTATAAT CGCTATAAGC    2160

AGAAACAATT ATTCTTAACA AAATGAATAC ACACAAGAAA AGCTTTAGTT TAGCTATTAG    2220
```

```
AACTAACTCT ATAATTATGA TAACCATGAG ATGCTGGAAC AGGAGCCAGC AGAAGCCACA      2280

GCCCTCTGAT ATTAATATAT AAAGAAACCA AAATCTGCTT GTTAAACTGA GGCAGTTGTA      2340

TGGATACTTC AACCTGAAAA TGCCCCCTTC TTCCTGAAAC AGAACATTTA ATAAAAATGG      2400

CATGCTTGGA CAGGAATTTC TTTTTTAAAA AATGCTTAGT TTTTATG                    2447

(2) INFORMATION FOR SEQ ID NO:13:

(i) SEQUENCE CHARACTERISTICS:
        (A) LENGTH: 830 base pairs
        (B) TYPE: nucleic acid
        (C) STRANDEDNESS: single
        (D) TOPOLOGY: linear (xi) SEQUENCE DESCRIPTION: SEQ ID NO:13:

TTCCTTTATC TCCTAGATAC ACCAAGATGA AGACTGCCAC CAACATCTAC ATTTTCAACC        60

TTGCTCTGCA GATGCCTTAG CCACCAGTAC CCTGCCCTTC CAGAGTGTGA ATTACCTAAT       120

GGGAACATGG CCATTTGGAA CCATCCTTTG CAAGATAGTG ATCTCCATAG ATTACTATAA       180

CATGTTCACC AGCATATTCA CCCTCTGCAC CATGAGTGTT GATCGATACA TTGCAGTCTG       240

CCACCCTGTC AAGGCCTTAG ATTTCCGTAC TCCCCNNNNN NNNNNNNNNN NNNNNNNNNN       300

NNNNNNNNNN NNNNNNNNNN NNNNNNNNNN NNNNNNNNNN NNNNNNNNNN NNNNNNNNNN       360

NNNNNNNNGT TCCATAGATT GTACACTAAC ATTCTCTCAT CCAACCTGGT ACTGGGAAAA       420

CCTGCTGAAG ATCTGTGTTT TCATCTTCGC CTTCATTATG CCAGTGCTCA TCATTACCGT       480

GTGCTATGGA CTGATGATCT TGCGCCTCAA GAGTGTCCGC ATGCTCTCTG GCTCCAAAGA       540

AAAGGACAGG AATCTTCGAA GGATCACCAG GATGGTGCTG GTGGTGGTGG CTGTGTTCAT       600

CGTCTGCTGG ACTCCCATTC ACATTTACGT CATCATTAAA GCCTTGGTTA CAATCCCAGA       660

AACTACGTTC CAGACTGTTT CTTGGCACTT CTGCATTGCT CTAGGTTACA CAAACAGCTG       720

CCTCAACCCA GTCCTTTATG CATTTCTGGA TGAAAACTTC CACGATGCTT CAGAGAGTTC       780

TGTATCCCAA CCTCTTCCAA CATTGAGCAA CAAAACTCCA CTCGAATTCC                 830

(2) INFORMATION FOR SEQ ID NO:14:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (xi) SEQUENCE DESCRIPTION: SEQ ID NO:14:

GGGTACCGGG CCCCCCCTCG AGGTCGACGG TATCGATAAG CTTGATATCG AATTCTTACT        60

GAATTAGGTA TCTTTCTTCA CACTACTTGG TAAAAAAAAT GAAAAGGCAG AAAAATTAGC       120

CCCAAAAGAG ATGAAACTCT TCCGTCCATC ACCATTGACT CTATTGTGAA CTTATGAAAA       180

AGGTAGTTGA GCAATATGAA GGCCATGATG TGGAATTAAA CACACACACA CACACACACA       240

CACACACACA CACATGCTGG ATTCTAAATG TGTCCTTCCT CCTCTCACTC TCTTGATTCA       300

AGTTTATTTC TGAACTGAGA CACGATCACC AC                                    332

(2) INFORMATION FOR SEQ ID NO:15:

(i) SEQUENCE CHARACTERISTICS:
        (A) LENGTH: 1981 base pairs
        (B) TYPE: nucleic acid
        (C) STRANDEDNESS: single
        (D) TOPOLOGY: linear
```

(xi) SEQUENCE DESCRIPTION: SEQ ID NO:15:

```
CGGATCCTTA GCATCCCCAA AGCGCCTCCG TGTACTTCTA AGGTGGGAGG GGGATACAAG      60
CAGAGGAGAA TATCGGACGC TCAGACGTTC CATTCTGCCT GCCGCTCTTC TCTGGTTCCA     120
CTAGGGCTTG TCCTTGTAAG AAACTGACGG AGCCTAGGGC AGCTGTGAGA GGAAGAGGCT     180
GGGGCGCCTG GAACCCGAAC ACTCTTGAGT GCTCTCAGTT ACAGNCTACC GAGTCCGCAG     240
GAAGCATTCA GAACCATGGA CAGCAGCGCC GGCCCAGGGA ACATCAGCGA CTGCTCTGAC     300
CCCTTAGCTC CTGCAAGTTG CTCCCCAGCA CCTGGCTCCT GGCTCAACTT GTCCCACGTT     360
GATGGAAACC AGTCCGACCC ATGCGGTCCT AACCCGACGG GCCTTGGCGG GAACGACAGC     420
CTGTGCCCTC AGACCGGCAG CCCTTCCATG GTCACAGCCA TCACCATCAT GGCCCTCTAT     480
TCTATCGTGT GTGTAGTGGG CCTCTTTGGA AACTTCCTGG TCATGTATGT GATTGTAAGA     540
TATACCAAAA TGAAGACTGC CACCAACATC TACATTTTCA ACCTTGCTCT GGCAGATGCC     600
TTAGCCACTA GCACGCTGCC CTTTCAGAGT GTTAACTACC TGATGGGAAC GTGGCCCTTT     660
GGAAACATCC TCTGCAAGAT CGTGATCTCA ATAGACTACT ACAACATGTT CACCAGTATC     720
TTCACCCTCT GCACCATGAG TGTAGACCGC TACATTGCCG TCTGCCACCC GGTCAAGGCC     780
CTGGATTTCC GTACCCCCCG AAATGCCAAA ATTGTCAATG TCTGCAACTG GATCCTCTCT     840
TCTGCCATTG GTCTGCCCGT AATGTTCATG GCAACCACAA AATACAGGCA GGGGTCCATA     900
GATTGCACCC TCACGTTCTC TCATCCCACA TGGTACTGGG AGAACCTGCT CAAAATCTGT     960
GTCTTCATCT TCGCCTTCAT CATGCCGGGC CTCATCATCA CTGTGTGTTA TGGACTGATG    1020
ATCTTACAGC TCAAGAGTGT CCGCATGCTG TCGGGCTCCA AGAAAAAGGA CAGGAACCTG    1080
CGCAGGATCA CCCGGATGGT GCTGGTGGTC GTGGCTGTAT TTATTGTCTG CTGGACCCCC    1140
ATCCACATCT ATGTCATCAT CAAAGCACTG ATCACGATTC AGAAACCAC TTTCCAGACT    1200
GTTTCCTGGC ACTTCTGCAT TGCCTTGGGT TACACAAACA GCTGCCTGAA CCCAGTTCTT    1260
TATGCGTTCC TGGATGAAAA CTTCAAACGA TGTTTTAGAG AGTTCTGCAT CCCAACTTCC    1320
TCCACAATCG AACAGCAAAA CTCTGCTCGA ATCCGTCAAA ACACTAGGGA ACACCCCTCC    1380
ACGGCTAATA CAGTGGATCG AACTAACCAC CAGCTAGAAA ATCTGGAAGC AGAAACTGCT    1440
CCATTGCCCT AACTGGGTCC CACGCCATCC AGACCCTCGC TAAACTTAGA GGCTGCCATC    1500
TACTTGGAAT CAGGTTGCTG TCAGGGTTTG TGGGAGGCTC TGGTTTCCTG GAAAAGCATC    1560
TGATCCTGCA TCATTCAAAG TCATTCCTCT CTGGCTATTC ACGCTACACG TCAGAGACAC    1620
TCAGACTGTG TCAAGCACTC AGAAGGAAGA GACTGCAGGC CACTACTGAA TCCAGCTCAT    1680
GTACAGAAAC ATCCAATGGA CCACAATACT CTGTGGTATG TGATTTGTGA TCAACATAGA    1740
AGGTGACCCT TCCCTATGTG GAATTTTTAA TTTCAAGGAA ATACTTATGA TCTCATCAAG    1800
GGAAAAATAG ATGTCACTTG TTAAATTCAC TGTAGTGATG CATAAAGGAA AAGCTACCTC    1860
TGACCTCTAG CCCAGTCACC CTCTATGGAA AGTTCCATAG GAATATGTG AGGGAAAATG     1920
TTGCTTCCAA ATTAAATTTT CACCTTTATG TTATAGTCTA GTTAAGACAT CAGGGGCATC    1980
T                                                                   1981
```

(2) INFORMATION FOR SEQ ID NO:16:

(i) SEQUENCE CHARACTERISTICS:
      (A) LENGTH: 398 amino acids
      (B) TYPE: amino acid
      (C) STRANDEDNESS: single
      (D) TOPOLOGY: linear (xi) SEQUENCE DESCRIPTION: SEQ ID NO:16:

Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Leu Asn Leu
                20                  25                  30

Ser His Val Asp Gly Asn Gln Ser Asp Pro Cys Gly Leu Asn Arg Thr
            35                  40                  45

Gly Leu Gly Gly Asn Asp Ser Leu Cys Pro Gln Thr Gly Ser Pro Ser
        50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
                100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Thr Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Ile Leu Ile Ile Thr Val Cys Tyr Gly Leu Met Ile
                245                 250                 255

Leu Arg Leu Lys Ser Val Arg Met Leu Ser Gly Ser Lys Glu Lys Asp
                260                 265                 270

Arg Asn Leu Arg Arg Ile Thr Arg Met Val Leu Val Val Val Ala Val
            275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
                340                 345                 350

Pro Thr Ser Ser Thr Ile Glu Gln Gln Asn Ser Thr Arg Val Arg Gln
            355                 360                 365

Asn Thr Arg Glu His Pro Ser Thr Ala Asn Thr Val Asp Arg Thr Asn
        370                 375                 380

His Gln Leu Glu Asn Leu Glu Ala Glu Thr Ala Pro Leu Pro
385                 390                 395

-continued (2) INFORMATION FOR SEQ ID NO:17:

(i) SEQUENCE CHARACTERISTICS:
        (A) LENGTH: 376 amino acids
        (B) TYPE: amino acid
        (C) STRANDEDNESS: single
        (D) TOPOLOGY: linear (xi) SEQUENCE DESCRIPTION: SEQ ID NO:17:

```
Met Glu Ser Pro Ile Gln Ile Phe Arg Gly Asp Gly Pro Thr Cys
 1               5                  10                  15

Ser Pro Ser Ala Cys Leu Leu Pro Asn Ser Ser Trp Phe Pro Asn
            20                  25                  30

Trp Ala Glu Ser Asp Ser Asn Gly Ser Val Gly Ser Glu Asp Gln Gln
            35                  40                  45

Leu Glu Ser Ala His Ile Ser Pro Ala Ile Pro Val Ile Ile Thr Ala
 50                  55                  60

Val Tyr Ser Val Val Phe Val Val Gly Leu Val Gly Asn Ser Leu Val
 65                  70                  75                  80

Met Phe Val Ile Ile Arg Tyr Thr Lys Met Lys Thr Ala Thr Asn Ile
                85                  90                  95

Tyr Ile Phe Asn Leu Ala Leu Ala Asp Ala Leu Val Thr Thr Thr Met
                100                 105                 110

Pro Phe Gln Ser Ala Val Tyr Leu Met Asn Ser Trp Pro Phe Gly Asp
            115                 120                 125

Val Leu Cys Lys Ile Val Ile Ser Ile Asp Tyr Tyr Asn Met Phe Thr
            130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ala Ser Ser Val Gly Ile Ser
                180                 185                 190

Ala Ile Val Leu Gly Gly Thr Lys Val Arg Glu Asp Val Ile Glu Cys
            195                 200                 205

Ser Leu Gln Phe Pro Asp Asp Glu Trp Trp Asp Leu Phe Met Lys Ile
210                 215                 220

Cys Val Phe Val Phe Ala Phe Val Ile Pro Val Leu Ile Ile Ile Val
225                 230                 235                 240

Cys Tyr Thr Leu Met Ile Leu Arg Leu Lys Ser Val Arg Leu Leu Ser
                245                 250                 255

Gly Ser Arg Glu Lys Asp Arg Asn Leu Arg Arg Ile Thr Lys Leu Val
            260                 265                 270

Leu Val Val Val Ala Val Phe Ile Ile Cys Trp Thr Pro Ile His Ile
            275                 280                 285

Phe Ile Leu Val Glu Ala Leu Gly Ser Thr Ser His Ser Thr Ala Ala
 290                 295                 300

Leu Ser Ser Tyr Tyr Phe Cys Ile Ala Leu Gly Tyr Thr Asn Ser Ser
305                 310                 315                 320

Leu Asn Pro Val Leu Tyr Ala Phe Leu Asp Glu Asn Phe Lys Arg Cys
                325                 330                 335

Phe Arg Asp Phe Cys Phe Pro Ile Lys Met Arg Met Glu Arg Gln Ser
            340                 345                 350

Thr Asn Arg Val Arg Asn Thr Val Gln Asp Pro Ala Ser Met Arg Asp
            355                 360                 365
```

```
Val Gly Gly Met Asn Lys Pro Val
    370             375
```

(2) INFORMATION FOR SEQ ID NO:18:

(i) SEQUENCE CHARACTERISTICS:
       (A) LENGTH: 1805 base pairs
       (B) TYPE: nucleic acid
       (C) STRANDEDNESS: double
       (D) TOPOLOGY: linear (ix) FEATURE:
        (A) NAME/KEY: CDS
        (B) LOCATION: 10..1119

(xi) SEQUENCE DESCRIPTION: SEQ ID NO:18:

```
GGCAGTGGC ATG GAG CCC CTC TTC CCC GCG CCG TTC TGG GAG GTT ATC           48
          Met Glu Pro Leu Phe Pro Ala Pro Phe Trp Glu Val Ile
              375                 380                 385

TAC GGC AGC CAC CTT CAG GGC AAC CTG TCC CTC CTG AGC CCC AAC CAC         96
Tyr Gly Ser His Leu Gln Gly Asn Leu Ser Leu Leu Ser Pro Asn His
                390                 395                 400

AGT CTG CTG CCC CCG CAT CTG CTG CTC AAT GCC AGC CAC GGC GCC TTC        144
Ser Leu Leu Pro Pro His Leu Leu Leu Asn Ala Ser His Gly Ala Phe
            405                 410                 415

CTG CCC CTC GGG CTC AAG GTC ACC ATC GTG GGG CTC TAC CTG GCC GTG        192
Leu Pro Leu Gly Leu Lys Val Thr Ile Val Gly Leu Tyr Leu Ala Val
            420                 425                 430

TGT GTC GGA GGG CTC CTG GGG AAC TGC CTT GTC ATG TAC GTC ATC CTC        240
Cys Val Gly Gly Leu Leu Gly Asn Cys Leu Val Met Tyr Val Ile Leu
        435                 440                 445

AGG CAC ACC AAA ATG AAG ACA GCC ACC AAT ATT TAC ATC TTT AAC CTG        288
Arg His Thr Lys Met Lys Thr Ala Thr Asn Ile Tyr Ile Phe Asn Leu
450                 455                 460                 465

GCC CTG GCC GAC ACT CTG GTC CTG CTG ACG CTG CCC TTC CAG GGC ACG        336
Ala Leu Ala Asp Thr Leu Val Leu Leu Thr Leu Pro Phe Gln Gly Thr
                470                 475                 480

GAC ATC CTC CTG GGC TTC TGG CCG TTT GGG AAT GCG CTG TGC AAG ACA        384
Asp Ile Leu Leu Gly Phe Trp Pro Phe Gly Asn Ala Leu Cys Lys Thr
            485                 490                 495

GTC ATT GCC ATT GAC TAC TAC AAC ATG TTC ACC AGC ACC TTC ACC CTA        432
Val Ile Ala Ile Asp Tyr Tyr Asn Met Phe Thr Ser Thr Phe Thr Leu
            500                 505                 510

ACT GCC ATG AGT GTG GAT CGC TAT GTA GCC ATC TGC CAC CCC ATC CGT        480
Thr Ala Met Ser Val Asp Arg Tyr Val Ala Ile Cys His Pro Ile Arg
        515                 520                 525

GCC CTC GAC GTC CGC ACG TCC AGC AAA GCC CAG GCT GTC AAT GTG GCC        528
Ala Leu Asp Val Arg Thr Ser Ser Lys Ala Gln Ala Val Asn Val Ala
530                 535                 540                 545

ATC TGG GCC CTG GCC TCT GTT GTC GGT GTT CCC GTT GCC ATC ATG GGC        576
Ile Trp Ala Leu Ala Ser Val Val Gly Val Pro Val Ala Ile Met Gly
                550                 555                 560

TCG GCA CAG GTC GAG GAT GAA GAG ATC GAG TGC CTG GTG GAG ATC CCT        624
Ser Ala Gln Val Glu Asp Glu Glu Ile Glu Cys Leu Val Glu Ile Pro
            565                 570                 575

ACC CCT CAG GAT TAC TGG GGC CCG GTG TTT GCC ATC TGC ATC TTC CTC        672
Thr Pro Gln Asp Tyr Trp Gly Pro Val Phe Ala Ile Cys Ile Phe Leu
            580                 585                 590

TTC TCC TTC ATC GTC CCC GTG CTC GTC ATC TCT GTC TGC TAC AGC CTC        720
Phe Ser Phe Ile Val Pro Val Leu Val Ile Ser Val Cys Tyr Ser Leu
        595                 600                 605

ATG ATC CGG CGG CTC CGT GGA GTC CGC CTG CTC TCG GGC TCC CGA GAG        768
```

```
Met Ile Arg Arg Leu Arg Gly Val Arg Leu Leu Ser Gly Ser Arg Glu
610                 615                 620                 625

AAG GAC CGG AAC CTG CGG CGC ATC ACT CGG CTG GTG CTG GTG GTA GTG      816
Lys Asp Arg Asn Leu Arg Arg Ile Thr Arg Leu Val Leu Val Val Val
                    630                 635                 640

GCT GTG TTC GTG GGC TGC TGG ACG CCT GTC CAG GTC TTC GTG CTG GCC      864
Ala Val Phe Val Gly Cys Trp Thr Pro Val Gln Val Phe Val Leu Ala
                645                 650                 655

CAA GGG CTG GGG GTT CAG CCG AGC AGC GAG ACT GCC GTG GCC ATT CTG      912
Gln Gly Leu Gly Val Gln Pro Ser Ser Glu Thr Ala Val Ala Ile Leu
                660                 665                 670

CGC TTC TGC ACG GCC CTG GGC TAC GTC AAC AGC TGC CTC AAC CCC ATC      960
Arg Phe Cys Thr Ala Leu Gly Tyr Val Asn Ser Cys Leu Asn Pro Ile
                675                 680                 685

CTC TAC GCC TTC CTG GAT GAG AAC TTC AAG GCC TGC TTC CGC AAG TTC     1008
Leu Tyr Ala Phe Leu Asp Glu Asn Phe Lys Ala Cys Phe Arg Lys Phe
690                 695                 700                 705

TGC TGT GCA TCT GCC CTG CGC CGG GAC GTG CAG GTG TCT GAC CGC GTG     1056
Cys Cys Ala Ser Ala Leu Arg Arg Asp Val Gln Val Ser Asp Arg Val
                710                 715                 720

CGC AGC ATT GCC AAG GAC GTG GCC CTG GCC TGC AAG ACC TCT GAG ACG     1104
Arg Ser Ile Ala Lys Asp Val Ala Leu Ala Cys Lys Thr Ser Glu Thr
                725                 730                 735

GTA CCG CGG CCC GCA TGACTAGGCG TGGACCTGCC CATGGTGCCT GTCAGCCCGC     1159
Val Pro Arg Pro Ala
            740

AGAGCCCATC TACGCCCAAC ACAGAGCTCA CACAGGTCAC TGCTCTCTAG GCGGACACAC   1219

CCTGGGCCCT GAGCATCCAG AGCCTGGGAT GGGCTTTTCC CTGTGGGCCA GGGATGCTCG   1279

GTCCCAGAGG AGGACCTAGT GACATCATGG GACAGGTCAA AGCATTAGGG CCACCTCCAT   1339

GGCCCCAGAC AGACTAAAGC TGCCCTCCTG GTGCAGGGCC GAGGGACAC AAGGACCTAC    1399

CTGGAAGCAG CTGACATGCT GGTGGACGGC CGTTACTGGA GCCCGTGCCC CTCCCTCCCC   1459

GTGCTTCATG TGACTCTTGG CCTCTCTGCT GCTGCGTTGG CAGAACCCTG GGTGGGCAGG   1519

CACCCGGAGG AGGAGCAGCA GCTGTGTCAT CCTGTGCCCC CCATGTGCTG TGTGCTGTTT   1579

GCATGGCAGG GCTCCAGCTG CCTTCAGCCC TGTGACGTCT CCTCAGGGCA GCTGGACAGG   1639

CTTGGCACGG CCCGGGAAGT GCAGCAGGCA GCTTTTCTTT GGGGTGGGAC TTGCCCTGAG   1699

CTTGGAGCTG CCACCTGGAG GACTTGCCTG TTCCGACTCC ACCTGTGCAG CCGGGGCCAC   1759

CCCAGGAGAA AGTGTCCAGG TGGGGGCTGG CAGTCCCTGG CTGCAG                 1805

(2) INFORMATION FOR SEQ ID NO:19:

(i) SEQUENCE CHARACTERISTICS:
        (A) LENGTH: 370 amino acids
        (B) TYPE: amino acid
        (D) TOPOLOGY: linear (ii) MOLECULE TYPE: protein (xi) SEQUENCE DESCRIPTION: SEQ ID NO:19:

Met Glu Pro Leu Phe Pro Ala Pro Phe Trp Glu Val Ile Tyr Gly Ser
1               5                   10                  15

His Leu Gln Gly Asn Leu Ser Leu Leu Ser Pro Asn His Ser Leu Leu
                20                  25                  30

Pro Pro His Leu Leu Leu Asn Ala Ser His Gly Ala Phe Leu Pro Leu
            35                  40                  45

Gly Leu Lys Val Thr Ile Val Gly Leu Tyr Leu Ala Val Cys Val Gly
```

```
              50                  55                  60
Gly Leu Leu Gly Asn Cys Leu Val Met Tyr Val Ile Leu Arg His Thr
 65                  70                  75                  80

Lys Met Lys Thr Ala Thr Asn Ile Tyr Ile Phe Asn Leu Ala Leu Ala
                 85                  90                  95

Asp Thr Leu Val Leu Leu Thr Leu Pro Phe Gln Gly Thr Asp Ile Leu
                100                 105                 110

Leu Gly Phe Trp Pro Phe Gly Asn Ala Leu Cys Lys Thr Val Ile Ala
                115                 120                 125

Ile Asp Tyr Tyr Asn Met Phe Thr Ser Thr Phe Thr Leu Thr Ala Met
130                 135                 140

Ser Val Asp Arg Tyr Val Ala Ile Cys His Pro Ile Arg Ala Leu Asp
145                 150                 155                 160

Val Arg Thr Ser Ser Lys Ala Gln Ala Val Asn Val Ala Ile Trp Ala
                165                 170                 175

Leu Ala Ser Val Val Gly Val Pro Val Ala Ile Met Gly Ser Ala Gln
                180                 185                 190

Val Glu Asp Glu Glu Ile Glu Cys Leu Val Glu Ile Pro Thr Pro Gln
                195                 200                 205

Asp Tyr Trp Gly Pro Val Phe Ala Ile Cys Ile Phe Leu Phe Ser Phe
210                 215                 220

Ile Val Pro Val Leu Val Ile Ser Val Cys Tyr Ser Leu Met Ile Arg
225                 230                 235                 240

Arg Leu Arg Gly Val Arg Leu Leu Ser Gly Ser Arg Glu Lys Asp Arg
                245                 250                 255

Asn Leu Arg Arg Ile Thr Arg Leu Val Leu Val Val Val Ala Val Phe
                260                 265                 270

Val Gly Cys Trp Thr Pro Val Gln Val Phe Val Leu Ala Gln Gly Leu
                275                 280                 285

Gly Val Gln Pro Ser Ser Glu Thr Ala Val Ala Ile Leu Arg Phe Cys
                290                 295                 300

Thr Ala Leu Gly Tyr Val Asn Ser Cys Leu Asn Pro Ile Leu Tyr Ala
305                 310                 315                 320

Phe Leu Asp Glu Asn Phe Lys Ala Cys Phe Arg Lys Phe Cys Cys Ala
                325                 330                 335

Ser Ala Leu Arg Arg Asp Val Gln Val Ser Asp Arg Val Arg Ser Ile
                340                 345                 350

Ala Lys Asp Val Ala Leu Ala Cys Lys Thr Ser Glu Thr Val Pro Arg
                355                 360                 365

Pro Ala
    370
```

(2) INFORMATION FOR SEQ ID NO:20:

(i) SEQUENCE CHARACTERISTICS:
        (A) LENGTH: 415 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: group(9, 12, 33, 40, 48)
        (D) OTHER INFORMATION: /note= "extracellular Asn residues
            that are consensus sites for N-linked glycosylation"

(xi) SEQUENCE DESCRIPTION: SEQ ID NO:20:

-continued

```
Met Asp Ser Ser Ala Pro Thr Asn Ala Ser Asn Cys Thr Asp Ala
1               5                  10                 15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
            35                  40                  45

Arg Thr Asn Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
                100                 105                 110

Ala Leu Ala Asp Ala Leu Ala Thr Ser Thr Leu Pro Phe Gln Ser Val
            115                 120                 125

Asn Tyr Leu Met Gly Thr Trp Pro Phe Gly Thr Ile Leu Cys Lys Ile
130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
            195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Val Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
    275                 280                 285

Ala Val Phe Ile Val Cys Trp Thr Pro Ile His Ile Tyr Val Ile Ile
290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
            355                 360                 365

Arg Gln Asn Thr Arg Asp His Pro Ser Thr Ala Asn Thr Val Asp Arg
    370                 375                 380

Thr Asn His Gln Leu Glu Asn Leu Glu Ala Glu Thr Ala Pro Leu Pro
385                 390                 395                 400

Phe Ile Gly Phe Ile Arg Ser Thr Ser Glu Gln Glu Asn Cys Glu
                405                 410                 415
```

(2) INFORMATION FOR SEQ ID NO:21:

(i) SEQUENCE CHARACTERISTICS:
        (A) LENGTH: 370 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: group(18, 33)
        (D) OTHER INFORMATION: /note= "extracellular Asn residues
            that are consensus sites for N-linked glycosylation"

(xi) SEQUENCE DESCRIPTION: SEQ ID NO:21:

```
Met Glu Pro Ala Pro Ser Ala Gly Ala Glu Leu Gln Pro Pro Leu Phe
1               5                   10                  15

Ala Asn Ala Ser Asp Ala Tyr Pro Ser Ala Cys Pro Ser Ala Gly Ala
            20                  25                  30

Asn Ala Ser Gly Pro Pro Ala Arg Ser Ala Ser Ser Leu Ala Leu Ala
        35                  40                  45

Ile Ala Ile Thr Ala Leu Tyr Ser Ala Val Cys Ala Val Gly Leu Ile
50                  55                  60

Gly Asn Val Leu Val Met Phe Gly Ile Val Arg Tyr Thr Lys Met Lys
65                  70                  75                  80

Thr Ala Thr Asn Ile Tyr Ile Phe Asn Leu Ala Leu Ala Asp Ala Leu
                85                  90                  95

Ala Thr Ser Thr Leu Pro Phe Gln Ser Ala Lys Tyr Leu Met Glu Thr
            100                 105                 110

Trp Pro Phe Gly Glu Leu Leu Cys Lys Ala Val Leu Ser Ile Asp Tyr
        115                 120                 125

Tyr Asn Met Phe Thr Ser Ile Phe Thr Leu Thr Met Met Ser Val Asp
130                 135                 140

Arg Tyr Ile Ala Val Cys His Pro Val Lys Ala Leu Asp Phe Arg Thr
145                 150                 155                 160

Pro Ala Lys Ala Lys Leu Ile Asn Ile Cys Ile Trp Val Leu Ala Ser
                165                 170                 175

Gly Val Gly Val Pro Ile Met Val Met Ala Val Thr Arg Pro Arg Asp
            180                 185                 190

Gly Ala Val Val Cys Met Leu Gln Phe Pro Ser Pro Ser Trp Tyr Trp
        195                 200                 205

Asp Thr Val Thr Lys Ile Cys Val Phe Leu Phe Ala Phe Val Val Pro
210                 215                 220

Ile Leu Ile Ile Thr Val Cys Tyr Gly Leu Met Leu Leu Arg Leu Arg
225                 230                 235                 240

Ser Val Arg Leu Leu Ser Gly Ser Lys Glu Lys Asp Arg Ser Leu Arg
                245                 250                 255

Arg Ile Thr Arg Met Val Leu Val Val Gly Ala Phe Val Val Cys
            260                 265                 270

Trp Ala Pro Ile His Ile Phe Val Ile Val Trp Thr Leu Val Asp Ile
        275                 280                 285

Arg Arg Asp Pro Leu Val Val Ala Ala Leu His Leu Cys Ile Ala Leu
290                 295                 300

Gly Tyr Ala Asn Ser Ser Leu Asn Pro Val Leu Tyr Ala Phe Leu Asp
305                 310                 315                 320

Glu Asn Phe Lys Arg Cys Phe Arg Gln Leu Cys Arg Lys Pro Cys Gly
                325                 330                 335
```

-continued

```
Arg Pro Asp Pro Ser Ser Phe Ser Arg Ala Arg Glu Ala Thr Ala Arg
            340                 345                 350

Glu Arg Val Thr Ala Cys Thr Pro Ser Asp Gly Pro Gly Gly Gly Ala
            355                 360                 365

Ala Ala
    370

(2) INFORMATION FOR SEQ ID NO:22:

(i) SEQUENCE CHARACTERISTICS:
        (A) LENGTH: 394 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: group(25, 39)
        (D) OTHER INFORMATION: /note= "extracellular Asn residues
            that are consensus sites for N-linked glycosylation"

(xi) SEQUENCE DESCRIPTION: SEQ ID NO:22:

Met Glu Ser Pro Ile Gln Ile Phe Arg Gly Asp Pro Gly Pro Thr Cys
1               5                  10                  15

Ser Pro Ser Ala Cys Leu Leu Pro Asn Ser Ser Ser Trp Phe Pro Asn
            20                  25                  30

Trp Ala Glu Ser Asp Ser Asn Gly Ser Val Gly Ser Glu Asp Gln Gln
            35                  40                  45

Leu Glu Ser Ala His Ile Ser Pro Ala Ile Pro Val Ile Ile Thr Ala
        50                  55                  60

Val Tyr Ser Val Val Phe Val Val Gly Leu Val Gly Asn Ser Leu Val
65                  70                  75                  80

Met Phe Val Ile Ile Arg Tyr Thr Lys Met Lys Thr Ala Thr Asn Ile
            85                  90                  95

Tyr Ile Phe Asn Leu Ala Leu Ala Asp Ala Leu Val Thr Thr Thr Met
            100                 105                 110

Pro Phe Gln Ser Ala Val Tyr Leu Met Asn Ser Trp Pro Phe Gly Asp
            115                 120                 125

Val Leu Cys Lys Ile Val Ile Ser Ile Asp Tyr Tyr Asn Met Phe Thr
        130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
            165                 170                 175

Ile Ile Asn Ile Cys Ile Trp Leu Leu Ala Ser Ser Val Gly Ile Ser
            180                 185                 190

Ala Ile Val Leu Gly Gly Thr Lys Val Arg Glu Asp Val Ile Glu Cys
        195                 200                 205

Ser Leu Gln Phe Pro Asp Asp Glu Trp Trp Asp Leu Phe Met Lys Ile
210                 215                 220

Cys Val Phe Val Phe Ala Phe Val Ile Pro Val Leu Ile Ile Ile Val
225                 230                 235                 240

Cys Tyr Thr Leu Met Ile Leu Arg Leu Lys Ser Val Arg Leu Leu Ser
            245                 250                 255

Gly Ser Arg Glu Lys Asp Arg Asn Leu Arg Arg Ile Thr Lys Leu Val
            260                 265                 270

Leu Val Val Val Ala Val Phe Ile Ile Cys Trp Thr Pro Ile His Ile
        275                 280                 285
```

```
Phe Ile Leu Val Glu Ala Leu Gly Ser Thr Ser His Ser Thr Ala Ala
            290                 295                 300

Leu Ser Ser Tyr Tyr Phe Cys Ile Ala Leu Gly Tyr Thr Asn Ser Ser
305                 310                 315                 320

Leu Asn Pro Val Leu Tyr Ala Phe Leu Asp Glu Asn Phe Lys Arg Cys
                325                 330                 335

Phe Arg Asp Phe Cys Phe Pro Ile Lys Met Arg Met Glu Arg Gln Ser
            340                 345                 350

Thr Asn Arg Val Arg Asn Thr Val Gln Asp Pro Ala Ser Met Arg Asp
                355                 360                 365

Val Gly Gly Met Asn Lys Pro Val Glu Gln Met His Glu Lys Ser Ile
            370                 375                 380

Pro Tyr Ser Gln Glu Thr Leu Val Val Asp
385                 390
```

(2) INFORMATION FOR SEQ ID NO:23:

(i) SEQUENCE CHARACTERISTICS:
        (A) LENGTH: 367 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: group(19, 26, 37)
        (D) OTHER INFORMATION: /note= "extracellular Asn residues
            that are consensus sites for N-linked glycosylation"

(xi) SEQUENCE DESCRIPTION: SEQ ID NO:23:

```
Met Glu Pro Leu Phe Pro Ala Pro Phe Trp Ile Tyr Gly Ser His Leu
1               5                   10                  15

Gln Gly Asn Leu Ser Leu Leu Ser Pro Asn His Ser Leu Leu Pro Pro
            20                  25                  30

His Leu Leu Leu Asn Ala Ser His Gly Ala Leu Pro Leu Gly Leu Lys
        35                  40                  45

Val Thr Ile Val Gly Leu Tyr Leu Ala Val Cys Val Gly Gly Leu Leu
    50                  55                  60

Gly Asn Cys Leu Val Met Tyr Val Leu Leu Arg His Thr Lys Met Lys
65                  70                  75                  80

Thr Ala Thr Asn Ile Tyr Ile Phe Asn Leu Ala Leu Ala Asp Thr Leu
                85                  90                  95

Val Leu Leu Thr Leu Pro Phe Gln Gly Thr Asp Ile Leu Leu Gly Pro
                100                 105                 110

Trp Pro Phe Gly Asn Ala Leu Cys Lys Thr Val Ile Ala Ile Asp Tyr
            115                 120                 125

Tyr Asn Met Phe Thr Ser Thr Phe Thr Leu Thr Ala Met Ser Val Asp
130                 135                 140

Arg Tyr Val Ala Ile Cys His Pro Ile Arg Ala Leu Asp Val Arg Thr
145                 150                 155                 160

Ser Ser Lys Ala Gln Ala Val Asn Val Ala Ile Trp Ala Leu Ala Ser
                165                 170                 175

Val Val Gly Val Pro Val Ala Ile Met Gly Ser Ala Gln Val Glu Asp
                180                 185                 190

Glu Glu Ile Glu Cys Leu Val Glu Ile Pro Thr Pro Gln Asp Tyr Trp
            195                 200                 205

Gly Pro Val Phe Ala Ile Cys Ile Phe Leu Phe Ser Phe Ile Val Pro
```

```
                210                 215                 220
Val Leu Val Ile Ser Val Cys Tyr Ser Leu Met Ile Arg Arg Leu Arg
225                 230                 235                 240

Gly Val Arg Leu Leu Ser Gly Ser Arg Glu Lys Asp Arg Asn Leu Arg
                245                 250                 255

Arg Ile Thr Arg Leu Val Leu Val Val Ala Val Phe Val Gly Cys
                260                 265                 270

Trp Thr Pro Val Gln Val Phe Val Leu Ala Gln Gly Leu Gly Val Gln
                275                 280                 285

Pro Ser Ser Glu Thr Ala Val Ala Ile Leu Arg Phe Cys Thr Ala Leu
                290                 295                 300

Gly Tyr Val Asn Ser Cys Leu Asn Pro Ile Leu Tyr Ala Phe Leu Asp
305                 310                 315                 320

Glu Asn Phe Lys Ala Cys Phe Arg Lys Phe Cys Cys Ala Ser Ala Leu
                325                 330                 335

Arg Arg Asp Val Gln Val Ser Asp Arg Val Arg Ser Ile Ala Lys Asp
                340                 345                 350

Val Ala Leu Ala Cys Lys Thr Ser Glu Thr Val Pro Arg Pro Ala
                355                 360                 365
```

(2) INFORMATION FOR SEQ ID NO:24:

(i) SEQUENCE CHARACTERISTICS:
        (A) LENGTH: 347 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 15
        (D) OTHER INFORMATION: /note= "extracellular Asn residue
            which is a consensus site for N-linked glycosylation"

(xi) SEQUENCE DESCRIPTION: SEQ ID NO:24:

```
Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
                20                  25                  30

Ala Ile Tyr Met Leu Val Phe Leu Leu Gly Thr Thr Gly Asn Gly Leu
                35                  40                  45

Val Leu Trp Thr Val Phe Arg Ser Ser Arg Lys Arg Arg Ser Ala Asp
50                  55                  60

Ile Phe Ile Ala Ser Leu Ala Val Ala Asp Leu Thr Phe Val Val Thr
65                  70                  75                  80

Leu Pro Leu Ala Thr Tyr Thr Tyr Arg Asp Tyr Asp Trp Pro Phe Gly
                85                  90                  95

Thr Phe Phe Cys Lys Leu Ser Ser Tyr Leu Ile Phe Val Asn Met Tyr
                100                 105                 110

Ala Ser Val Phe Cys Leu Thr Gly Leu Ser Phe Asp Arg Tyr Leu Ala
                115                 120                 125

Ile Val Arg Pro Val Ala Asn Ala Arg Leu Arg Leu Arg Val Ser Gly
                130                 135                 140

Ala Val Ala Thr Ala Val Leu Trp Val Leu Ala Ala Leu Leu Ala Met
145                 150                 155                 160

Pro Val Met Val Leu Thr Thr Gly Asp Leu Glu Asn Thr Thr Val Gln
                165                 170                 175
```

```
Cys Tyr Met Asp Tyr Ser Ser Ser Glu Trp Ala Trp Glu Val Gly Leu
            180                 185                 190

Gly Val Ser Ser Thr Thr Val Gly Phe Val Val Pro Phe Thr Ile Met
        195                 200                 205

Leu Thr Cys Tyr Phe Phe Ile Ala Gln Thr Ile Ala Gly His Phe Arg
    210                 215                 220

Lys Glu Arg Ile Glu Gly Leu Arg Lys Arg Arg Arg Leu Leu Ser Ile
225                 230                 235                 240

Ile Val Val Leu Val Val Thr Phe Ala Leu Cys Trp Met Pro Tyr His
                245                 250                 255

Leu Tyr Met Leu Gly Ser Leu Leu His Trp Pro Cys Asp Asp Leu Phe
            260                 265                 270

Leu Met Asn Ile Phe Pro Tyr Cys Thr Cys Ile Ser Tyr Val Asn Ser
        275                 280                 285

Cys Leu Asn Pro Phe Leu Tyr Ala Phe Phe Asp Pro Arg Phe Arg Ala
    290                 295                 300

Cys Thr Ser Met Leu Cys Cys Gly Gln Ser Arg Cys Ala Gly Thr Ser
305                 310                 315                 320

His Ser Ser Ser Gly Glu Lys Ser Ala Ser Tyr Ser Ser Gly His Ser
                325                 330                 335

Gln Gly Pro Gly Pro Asn Met Gly Lys Gly Gly
            340                 345
```

(2) INFORMATION FOR SEQ ID NO:25:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:25:

```
Tyr Gly Gly Phe Xaa
1               5
```